US011219608B2

(12) United States Patent
Apkarian et al.

(10) Patent No.: US 11,219,608 B2
(45) Date of Patent: Jan. 11, 2022

(54) TRIPLE COMBINATION FORMULATION FOR TREATMENT OF CHRONIC PAIN

(71) Applicants: Northwestern University, Evanston, IL (US); The University of Notre Dame Du Lac, South Bend, IN (US)

(72) Inventors: A. Vania Apkarian, Chicago, IL (US); Kasturi Haldar, Chicago, IL (US); Suhail Alam, Mishawaka, IN (US); Maria Virginia Centeno, Chicago, IL (US)

(73) Assignees: Northwestern University, Evanston, IL (US); The University of Notre Dame Du Lac, South Bend, IN (US)

( * ) Notice: Subject to any disclaimer, the term of this patent is extended or adjusted under 35 U.S.C. 154(b) by 0 days.

(21) Appl. No.: 16/209,261

(22) Filed: Dec. 4, 2018

(65) Prior Publication Data

US 2019/0167610 A1    Jun. 6, 2019

Related U.S. Application Data

(60) Provisional application No. 62/594,216, filed on Dec. 4, 2017.

(51) Int. Cl.
| | |
|---|---|
| *A61K 31/167* | (2006.01) |
| *A61K 47/40* | (2006.01) |
| *A61K 47/10* | (2017.01) |
| *A61P 25/02* | (2006.01) |
| *A61P 25/04* | (2006.01) |
| *A61K 47/60* | (2017.01) |
| *A61K 45/06* | (2006.01) |
| *A61P 25/00* | (2006.01) |
| *A61K 9/00* | (2006.01) |

(52) U.S. Cl.
CPC ............ *A61K 31/167* (2013.01); *A61K 45/06* (2013.01); *A61K 47/10* (2013.01); *A61K 47/40* (2013.01); *A61K 47/60* (2017.08); *A61P 25/00* (2018.01); *A61P 25/02* (2018.01); *A61P 25/04* (2018.01); *A61K 9/0019* (2013.01); *A61K 9/0053* (2013.01)

(58) Field of Classification Search
CPC ...... A61K 31/167; A61K 47/60; A61K 45/06; A61K 47/40; A61K 47/10; A61K 9/0019; A61K 9/0053; A61P 25/00; A61P 25/02; A61P 25/04
See application file for complete search history.

(56) References Cited

U.S. PATENT DOCUMENTS

2015/0359762 A1    12/2015    Haldar et al.

FOREIGN PATENT DOCUMENTS

WO    2015191931    12/2015

OTHER PUBLICATIONS

Alam et al, 2017, bioRxiv (doi: doi.org/10.1101/191635).
Alam, et al. Genomic Expression Analyses Reveal Lysosomal, Innate Immunity Proteins, as Disease Correlates in Murine Models of a Lysosomal Storage Disorder. Plos One 7, doi:ARTN e4827310. 1371/journal.pone.0048273 (2012).
Alam, et al. Plasma signature of neurological disease in the monogenetic disorder Niemann-Pick Type C. J Biol Chem 289, 8051-8066, doi:10.1074/jbc.M113.526392 (2014).
Alam, et al., Chronic administration of an HDAC inhibitor treats both neurological and systemic Niemann-Pick type C disease in a mouse model. Science translational medicine 8, 326ra323, doi:10.1126/scitranslmed.aad9407 (2016).
Alobaidy, Recent advances in the diagnosis and treatment of niemann-pick disease type C in children: a guide to early diagnosis for the general pediatrician. Int J Pediatr 2015, 816593, doi:10.1155/2015/816593 (2015).
Alvarado, et al. An epigenetic hypothesis for the genomic memory of pain. Front Cell Neurosci 9, 88, doi:10.3389/fncel.2015.00088 (2015).
Anders, et al., Differential expression analysis for sequence count data. Genome Biol 11, doi:ARTN R106 10.1186/gb-2010-11-10-r106 (2010).
Apkarian, et al., Chronic pain patients are impaired on an emotional decision-making task Pain 108, 129-136 (2004).
Apkarian, et al., Role of adult hippocampal neurogenesis in persistent pain. Pain 157, 418-428, doi:10.1097/j.pain.0000000000000332 (2016).
Aqul, et al., Unesterified cholesterol accumulation in late endosomes/lysosomes causes neurodegeneration and is prevented by driving cholesterol export from this compartment. J Neurosci 31, 9404-9413, doi: 10.1523/ineurosci.1317-11.2011 (2011).
Bai, et al., Inhibition of class II histone deacetylases in the spinal cord attenuates inflammatory hyperalgesia. Molecular pain 6, 51, doi:10.1186/1744-8069-6-51 (2010).
Baliki, et al., Nociception, Pain, Negative Moods, and Behavior Selection. Neuron 87, 474-491, doi: 10.1016/j.neuron.2015.06.005 (2015).
Baliki, et al., Corticostriatal functional connectivity predicts transition to chronic back pain. Nature neuroscience 15, 1117-1119, doi:10.1038/nn.3153 (2012).
Baliki, et al., Resting-sate functional reorganization of the rat limbic system following neuropathic injury. Scientific reports 4, 6186, doi:10.1038/srep06186 (2014).
Baliki, et al., Predicting value of pain and analgesia: nucleus accumbens response to noxious stimuli changes in the presence of chronic pain. Neuron 66, 149-160, doi:S0896-6273(10)00171-6 [pii] 10.1016/j.neuron.2010.03.002 (2010).

(Continued)

*Primary Examiner* — Sahar Javanmard
(74) *Attorney, Agent, or Firm* — Quarles & Brady LLP

(57) ABSTRACT

The disclosure relates to use of a triple formulation comprising a histone deacetylase, a cyclodextrin and polyethylene glycol or propylene glycol, and in the treatment and management of chronic pain.

12 Claims, 21 Drawing Sheets
(17 of 21 Drawing Sheet(s) Filed in Color)

(56) References Cited

OTHER PUBLICATIONS

Breivik, et al., Survey of chronic pain in Europe: prevalence, impact on daily life, and treatment. Eur J Pain 10, 287-333, doi:10.1016/j.ejpain.2005.06.009 (2006).
Calamini, et al., Protein Homeostasis as a Therapeutic Target for Diseases of Protein Conformation. Current Topics in Medicinal Chemistry 12, 2623-2640 (2012).
Carstea, et al., Niemann-Pick C1 disease gene: homology to mediators of cholesterol homeostasis. Science 277, 228-231 (1997).
Chang, et al., Novel method for functional brain imaging in awake minimally restrained rats. Journal of neurophysiology 116, 61-80, doi:10.1152/jn.01078.2015 (2016).
Chang, et al., Role of nucleus accumbens in neuropathic pain: linked multi-scale evidence in the rat transitioning to neuropathic pain. Pain 155, 1128-1139, doi:10.1016/j.pain.2014.02.019 (2014).
Cherng, et al., Baicalin ameliorates neuropathic pain by suppressing HDAC1 expression in the spinal cord of spinal nerve ligation rats. J Formos Med Assoc 113, 513-520, doi:10.1016/j.jfma.2013.04.007 (2014).
Chessum, et al., M. Recent advances in cancer therapeutics. Prog Med Chem 54, 1-63, doi:10.1016/bs.pmch.2014.11.002 (2015).
Chiechio, et al., Epigenetic modulation of mGlu2 receptors by histone deacetylase inhibitors in the treatment of inflammatory pain. Mol Pharmacol 75, 1014-1020, doi:10.1124/mol.108.054346 (2009).
Chitnis, et al., CNS inflammation and neurodegeneration. The Journal of Clinical Investigation 127, doi: 10.1172/JCI90609 (2017).
Davis, et al., Identifying brain nociceptive information transmission in patients with chronic somatic pain. Pain reports 1, e575-e577 (2016).
Decosterd, et al., Spared nerve injury: an animal model of persistent peripheral neuropathic pain. Pain 87, 149-158 (2000).
Descalzi, et al., Epigenetic mechanisms of chronic pain. Trends in neurosciences 38, 237-246, doi:10.1016/j.tins.2015.02.001 (2015).
Di, et al., SAHA Enhances Proteostasis of Epilepsy-Associated alpha 1(A322D)beta 2 gamma 2 GABA(A) Receptors. Chem Biol 20, 1456-1468, doi:10.1016/j.chembiol.2013.09.020 (2013).
Dillies, et al., A comprehensive evaluation of normalization methods for Illumina high-throughput RNA sequencing data analysis. Brief Bioinform 14, 671-683, doi:10.1093/bib/bbs046 (2013).
Dokmanovic, et al., Histone deacetylase inhibitors: Overview and perspectives. Mol Cancer Res 5, 981-989, doi:10.1158/1541-7786. Mcr-07-0324 (2007).
Falkenberg, et al., Histone deacetylases and their inhibitors in cancer, neurological diseases and immune disorders (vol. 13, p. 673, 2014). Nature Reviews Drug Discovery 14, 219-219, doi:10.1038/nrd4579 (2015).
Fischer, et al., Hematoxylin and eosin staining of tissue and cell sections. CSH protocols 2008, pdb.prot4986, doi:10.1101/pdb.prot4986 (2008).
Giannini, et al., Histone deacetylase inhibitors in the treatment of cancer: overview and perspectives. Future Med Chem 4, 1439-1460, doi:10.4155/Fmc.12.80 (2012).
Griese, et al., Respiratory disease in Niemann-Pick type C2 is caused by pulmonary alveolar proteinosis. Clinical genetics 77, 119-130, doi:10.1111/j.1399-0004.2009.01325.x (2010).
Guillemot, et al., Lung disease in Niemann-Pick disease. Pediatric pulmonology 42, 1207-1214, doi: 10.1002/ppul.20725 (2007).
Harstall, et al., How prevalent is chronic pain? Pain Clinical Updates 11 (2003). (http://www.iasp- pain.org/PublicationsNews/NewsletterIssue.aspx?ItemNumber=2136).
Hashmi, et al., Shape shifting pain: chronification of back pain shifts brain representation from nociceptive to emotional circuits. Brain : a journal of neurology 136, 2751-2768, doi:10.1093/brain/awt211 (2013).
Imai, et al., Change in microRNAs associated with neuronal adaptive responses in the nucleus accumbens under neuropathic pain. The Journal of neuroscience : the official journal of the Society for Neuroscience 31, 15294-15299, doi:10.1523/JNEUROSCI.0921-11.2011 (2011).

Wraith, et al., Miglustat in adult and juvenile patients with Niemann-Pick disease type C: Long-term data from a clinical trial. Mol. Genet. Metab. 99, 351-357 (2010).
Jiang, et al., Development of a bile acid-based newborn screen for Niemann-Pick disease type C. Science translational medicine 8, 337ra363, doi:10.1126/scitranslmed.aaf2326 (2016).
Kelly, et al., Phase I clinical trial of histone deacetylase inhibitor: suberoylanilide hydroxamic acid administered intravenously. Clin Cancer Res 9, 3578-3588 (2003).
Kennedy, et al., Presymptomatic Alterations in Amino Acid Metabolism and DNA Methylation in the Cerebellum of a Murine Model of Niemann-Pick Type C Disease. The American journal of pathology 186, 1582-1597, doi:10.1016/j.ajpath.2016.02.012 (2016).
Khangura, et al., Histone acetylation and histone deacetylation in neuropathic pain: An unresolved puzzle? European journal of pharmacology 795, 36-42, doi:10 1016/j.ejphar.2016.12.001 (2017).
Kirkegaard, et al., Heat shock protein-based therapy as a potential candidate for treating the sphingolipidoses. Science translational medicine 8, 355ra118, doi:10.1126/scitranslmed.aad9823 (2016).
Lee, et al., Activation of corticostriatal circuitry relieves chronic neuropathic pain. The Journal of neuroscience : the official journal of the Society for Neuroscience 35, 5247-5259, doi:10.1523/JNEUROSCI.3494-14.2015 (2015).
Liu, et al., Reversal of defective lysosomal transport in NPC disease ameliorates liver dysfunction and neurodegeneration in the npc1−/− mouse. Proc Natl Acad Sci U S A 106, 2377-2382, doi:10.1073/pnas.0810895106 (2009).
Liu, et al., Phosphoinositide phosphatases in cell biology and disease. Prog Lipid Res 49, 201-217 (2010).
Lyseng-Williamson, Miglustat: a review of its use in Niemann-Pick disease type C. Drugs 74, 61-74, doi: 10.1007/s40265-013-0164-6 (2014).
MacCoun, Blind analysis: Hide results to seek the truth. . Nature 526, 187-189 (2015).
Machelska, et al., Recent advances in understanding neuropathic pain: glia, sex differences, and epigenetics. F1000Research 5, 2743, doi:10.12688/f1000research.9621.1 (2016).
Mansour, et al., Global disruption of degree rank order: a hallmark of chronic pain. Scientific reports 6, 34853, doi:10.1038/srep34853 (2016).
Mansour, et al., Brain white matter structural properties predict transition to chronic pain. Pain 154, 2160-2168, doi:10.1016/j.pain.2013.06.044 (2013).
Massart, et al., Overlapping signatures of chronic pain in the DNA methylation landscape of prefrontal cortex and peripheral T cells. Scientific reports 6, 19615, doi:10.1038/srep19615 (2016).
Maue, et al., A novel mouse model of Niemann-Pick type C disease carrying a D1005G-Npc1 mutation comparable to commonly observed human mutations. Human Molecular Genetics 21, 730-750, doi:10. 1093/hmg/ddr505 (2012).
Millecamps, et al., D-cycloserine reduces neuropathic pain behavior through limbic NMDA-mediated circuitry. Pain (2006).
Monteiro et al.,et al. Cyclodextrin-Based Delivery Systems for Arthritic Diseases: From Development to Experimental Therapeutics. Curr Pharm Des 21, 4907-4916 (2015).
Montgomery, et al., Histone deacetylases 1 and 2 control the progression of neural precursors to neurons during brain development. Proc Natl Acad Sci U S A 106, 7876-7881, doi:10.1073/pnas.0902750106 (2009).
Moore, et al., Partial peripheral nerve injury promotes a selective loss of GABAergic inhibition in the superficial dorsal horn of the spinal cord. J Neurosci. 22, 6724-6731 (2002).
Mottamal, et al., Histone Deacetylase Inhibitors in Clinical Studies as Templates for New Anticancer Agents. Molecules 20, 3898-3941, doi:10.3390/molecules20033898 (2015).
Murray, et al., Measuring the global burden of disease. The New England journal of medicine 369, 448-457, doi:10.1056/NEJMra1201534 (2013).
Mutso, et al., Abnormalities in hippocampal functioning with persistent pain. The Journal of neuroscience : the official journal of the Society for Neuroscience 32, 5747-5756, doi:10.1523/JNEUROSCI.0587-12.2012 (2012).

(56) References Cited

OTHER PUBLICATIONS

Mutso, et al., Reorganization of Hippocampal Functional Connectivity with Transition to Chronic Back Pain. Journal of neurophysiology, doi:10.1152/jn.00611.2013 (2013).
Nagral, Gaucher disease. Journal of clinical and experimental hepatology 4, 37-50, doi:10.1016/j.jceh.2014.02.005 (2014).
Nascimento, et al., Neuropathic Pain Treatment: Still a Challenge. Neurol Int 8, 6322, doi:10.4081/ni.2016.6322 (2016).
Naureckiene, et al., Identification of HE1 as the second gene of Niemann-Pick C disease. Science 290, 2298-2301 (2000).
Norwood, et al., Histone deacetylase 3 is necessary for proper brain development. J Biol Chem 289, 34569-34582, doi:10.1074/jbc.M114.576397 (2014).
Ory, et al., Intrathecal 2-hydroxypropyl-beta-cyclodextrin decreases neurological disease progression in Niemann-Pick disease, type C1: a non-randomised, open-label, phase 1-2 trial. Lancet, doi:10.1016/s0140-6736(17)31465-4 (2017).
Pineda, et al., Clinical experience with miglustat therapy in pediatric patients with Niemann-Pick disease type C: a case series. Molecular genetics and metabolism 99, 358-366, doi:10.1016/j.ymgme.2009.11.007 (2010).
Pontikis, et al., Cyclodextrin alleviates neuronal storage of cholesterol in Niemann-Pick C disease without evidence of detectable blood-brain barrier permeability. J. Inherit. Metab. Dis. 36, 491-498 (2013).
Porter, et al., Cholesterol oxidation products are sensitive and specific blood-based biomarkers for Niemann-Pick C1 disease. Science translational medicine 2, 56ra81, doi:10.1126/scitranslmed.3001417 (2010).
Ramirez, et al., Quantitative role of LAL, NPC2, and NPC1 in lysosomal cholesterol processing defined by genetic and pharmacological manipulations. Journal of lipid research 52, 688-698, doi:10.1194/jlr.M013789 (2011).
Ramirez, et al., Weekly cyclodextrin administration normalizes cholesterol metabolism in nearly every organ of the Niemann-Pick type C1 mouse and markedly prolongs life. Pediatr Res 68, 309-315, doi:10.1203/00006450-201011001-0060410.1203/PDR.0b013e3181ee4dd2 (2010).
Ransohoff, How neuroinflammation contributes to neurodegeneration. Science 353, 777-783, doi:10.1126/science.aag2590 (2016).
Ren, et al., The indirect pathway of the nucleus accumbens shell amplifies neuropathic pain. Nature neuroscience 19, 220-222, doi:10.1038/nn.4199 (2016).
Roche, et al., Inside HDACs with more selective HDAC inhibitors. Eur J Med Chem 121, 451-483, doi:10.1016/j.ejmech.2016.05.047 (2016).
Rossi, et al., Current options for drug delivery to the spinal cord. Expert Opin Drug Deliv 10, 385-396, doi:10.1517/17425247.2013.751372 (2013).
Scholz, et al., Blocking caspase activity prevents transsynaptic neuronal apoptosis and the loss of inhibition in lamina II of the dorsal horn after peripheral nerve injury. J Neurosci. 25, 7317-7323 (2005).
Simon, et al., KATching-Up on Small Molecule Modulators of Lysine Acetyltransferases. J Med Chem 59, 1249-1270, doi:10.1021/acs.jmedchem.5b01502 (2016).
Slotkin, et al., Sustained Local Release of Methylprednisolone From a Thiol-Acrylate Poly(Ethylene Glycol) Hydrogel for Treating Chronic Compressive Radicular Pain. Spine 41, E441-448, doi:10.1097/BRS.0000000000001309 (2016).
Small, et al., Increased taste intensity perception exhibited by patients with chronic back pain. Pain 120, 124-130 (2006).
Subramanian, et al., Quantitative Analysis of the Proteome Response to the Histone Deacetylase Inhibitor (HDACi) Vorinostat in Niemann-Pick Type C1 disease. Molecular & cellular proteomics : MCP, doi:10.1074/mcp.M116.064949 (2017).
Tajerian, et al., Peripheral nerve injury is associated with chronic, reversible changes in global DNA methylation in the mouse prefrontal cortex. PloS one 8, e55259, doi:10.1371/journal.pone.0055259 (2013).
Torres-Perez, et al., Phosphorylated Histone 3 at Serine 10 Identifies Activated Spinal Neurons and Contributes to the Development of Tissue Injury-Associated Pain. Scientific reports 7, 41221, doi:10.1038/srep41221 (2017).
Tran, et al., Epigenetic modulation of chronic anxiety and pain by histone deacetylation. Molecular psychiatry 20, 1219-1231, doi:10.1038/mp.2014.122 (2015).
Vachon-Presseau, et al., Corticolimbic anatomical characteristics predetermine risk for chronic pain. Brain : a journal of neurology In Press, doi:10.1093/brain/aww100 (2016).
Vachon-Presseau, et al., The Emotional Brain as a Predictor and Amplifier of Chronic Pain. J Dent Res 95, 605-612, doi:10.1177/0022034516638027 (2016).
Vanier, Niemann-Pick disease type C. Orphanet J Rare Dis 5, 16, doi:10.1186/1750-1172-5-16 (2010).
Venkatraman, et al., The histone deacetylase HDAC3 is essential for Purkinje cell function, potentially complicating the use of HDAC inhibitors in SCA1. Hum Mol Genet 23, 3733-3745, doi:10.1093/hmg/ddu081 (2014).
Vite, et al., Intracisternal cyclodextrin prevents cerebellar dysfunction and Purkinje cell death in feline Niemann-Pick type C1 disease. Science translational medicine 7, 276ra226, doi:10.1126/scitranslmed.3010101 (2015).
Volmar, et al., Histone deacetylases (HDACs) and brain function. Neuroepigenetics 1, 20-27, doi:https://doi.org/10.1016/j.nepig.2014.10.002 (2015).
Wang, et al., Is there any therapeutic value for the use of histone deacetylase inhibitors for chronic pain? Brain research bulletin 125, 44 52, doi:10.1016/j.brainresbull.2016.04.010 (2016).
Winston, et al., Chronic prenatal stress epigenetically modifies spinal cord BDNF expression to induce sex-specific visceral hypersensitivity in offspring. Neurogastroenterol Motil 26, 715-730, doi:10.1111/nmo.12326 (2014).
Xie, et al., Amino acid substitution in NPC1 that abolishes cholesterol binding reproduces phenotype of complete NPC1 deficiency in mice. Proc. Natl. Acad. Sci. U.S.A. 108, 15330-15335 (2011).
Xu, et al., Histone deacetylase inhibitors: molecular mechanisms of action. Oncogene 26, 5541-5552, doi:10.1038/sj.onc.1210620 (2007).
Yang, et al., Histone deacetylase inhibitors increase glucocerebrosidase activity in Gaucher disease by modulation of molecular chaperones. Proceedings of the National Academy of Sciences of the United States of America 110, 966-971, doi:10.1073/pnas.1221046110 (2013).
Yanjanin, et al., Linear clinical progression, independent of age of onset, in Niemann-Pick disease, type C. American journal of medical genetics. Part B, Neuropsychiatric genetics : the official publication of the International Society of Psychiatric Genetics 153b, 132-140, doi:10.1002/ajmg.b.30969 (2010).
Yu, et al., Npc1 acting in neurons and glia is essential for the formation and maintenance of CNS myelin. PLoS Genet 9, e1003462, doi:10.1371/journal.pgen.1003462 (2013).
Zammataro, et al., HDAC and HAT inhibitors differently affect analgesia mediated by group II metabotropic glutamate receptors. Molecular pain 10, 68, doi:10.1186/1744-8069-10-68 (2014).
Zhang, et al., Epigenetic suppression of GAD65 expression mediates persistent pain. Nat Med 17, 1448-1455, doi:10.1038/nm.2442 (2011).

FIG. 13

| TCF-Treated | Assesment#1 | Assesment#2 | Assesment#3 | Assesment#4 | | |
|---|---|---|---|---|---|---|
| Mouse ID | CN235 | CN235 | CN235 | CN235 | | |
| Gender | Male | Male | Male | Male | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 0 | 1 | 1 | | |
| Limb Tone | 0 | 0 | 0 | 0 | | |
| Weight score | 0 | 0 | 0 | 0 | | |
| Total Score | 0 | 0 | 1 | 1 | | |

| TCF-Treated | Assesment#1 | Assesment#2 | Assesment#3 | Assesment#4 | | |
|---|---|---|---|---|---|---|
| Mouse ID | CN238 | CN238 | CN238 | CN238 | | |
| Gender | Male | Male | Male | Male | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 0 | 0 | 0 | | |
| Limb Tone | 0 | 0 | 0 | 0 | | |
| Weight score | 0 | 0 | 0 | 0 | | |
| Total Score | 0 | 0 | 0 | 0 | | |

| TCF-Treated | Assesment#1 | Assesment#2 | Assesment#3 | Assesment#4 | | |
|---|---|---|---|---|---|---|
| Mouse ID | CN239 | CN239 | CN239 | CN239 | | |
| Gender | Male | Male | Male | Male | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 1 | 1 | 1 | | |
| Limb Tone | 1 | 0 | 0 | 0 | | |
| Weight score | 1 | 1 | 0 | 0 | | |
| Total Score | 2 | 2 | 1 | 1 | | |

| TCF-Treated | Assesment#1 | Assesment#2 | Assesment#3 | Assesment#4 | | |
|---|---|---|---|---|---|---|
| Mouse ID | CN245 | CN245 | CN245 | CN245 | | |
| Gender | Female | Female | Female | Female | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 0 | 1 | 1 | | |
| Limb Tone | 0 | 0 | 0 | 0 | | |

FIG. 13 CONTINUED

| | | | | | | |
|---|---|---|---|---|---|---|
| Weight score | 0 | 0 | 0 | 1 | | |
| Total Score | 0 | 0 | 1 | 2 | | |
| | | | | | | |
| TCF-Treated | Assesment#1 | Assesment#2 | Assesment#3 | Assesment#4 | | |
| Mouse ID | CN246 | CN246 | CN246 | CN246 | | |
| Gender | Female | Female | Female | Female | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 0 | 1 | 1 | | |
| Limb Tone | 0 | 0 | 0 | 0 | | |
| Weight score | 0 | 0 | 1 | 0 | | |
| Total Score | 0 | 0 | 2 | 1 | | |
| | | | | | | |
| TCF-Treated | Assesment#1 | Assesment#2 | Assesment#3 | Assesment#4 | | |
| Mouse ID | CN247 | CN247 | CN247 | CN247 | | |
| DOB | 10/10/2016 | 10/10/2016 | 10/10/2016 | 10/10/2016 | | |
| Gender | Female | Female | Female | Female | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 0 | 1 | 1 | | |
| Limb Tone | 0 | 0 | 0 | 0 | | |
| Weight score | 0 | 0 | 0 | 1 | | |
| Total Score | 0 | 0 | 1 | 2 | | |
| | | | | | | |
| TCF-Treated | Assesment#1 | Assesment#2 | Assesment#3 | Assesment#4 | | |
| Mouse ID | CN248 | CN248 | CN248 | CN248 | | |
| Gender | Female | Female | Female | Female | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 0 | 1 | 1 | | |
| Limb Tone | 0 | 0 | 0 | 0 | | |
| Weight score | 0 | 0 | 0 | 1 | | |
| Total Score | 0 | 0 | 1 | 2 | | |
| | | | | | | |
| TCF-Treated | Assesment#1 | Assesment#2 | Assesment#3 | Assesment#4 | | |
| Mouse ID | CN249 | CN249 | CN249 | CN249 | | |
| Gender | Female | Female | Female | Female | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |

FIG. 13 CONTINUED

| | | | | | | |
|---|---|---|---|---|---|---|
| Grooming | 0 | 0 | 1 | 1 | | |
| Limb Tone | 0 | 0 | 0 | 0 | | |
| Weight score | 0 | 0 | 0 | 0 | | |
| Total Score | 0 | 0 | 1 | 1 | | |
| | | | | | | |
| TCF-Treated | Assesment#1 | Assesment#2 | Assesment#3 | Assesment#4 | Assesment#5 | Assesment#6 |
| Mouse ID | CN240 | CN240 | CN240 | CN240 | CN240 | CN240 |
| Gender | Male | Male | Male | Male | Male | Male |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 1 | 1 | 2 | 2 | 2 |
| Limb Tone | 1 | 0 | 0 | 0 | 0 | 0 |
| Weight score | 0 | 0 | 0 | 0 | 0 | 0 |
| Total Score | 1 | 1 | 1 | 2 | 2 | 2 |

| | | | | | | |
|---|---|---|---|---|---|---|
| TCF-Treated | Assesment#1 | Assesment#2 | Assesment#3 | Assesment#4 | Assesment#5 | Assesment#6 |
| Mouse ID | CN241 | CN241 | CN241 | CN241 | CN241 | CN241 |
| Gender | Male | Male | Male | Male | Male | Male |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 1 | 1 | 2 | 2 | 2 |
| Limb Tone | 0 | 0 | 0 | 0 | 0 | 0 |
| Weight score | 0 | 0 | 0 | 0 | 0 | 0 |
| Total Score | 0 | 1 | 1 | 2 | 2 | 2 |
| | | | | | | |
| TCF-Treated | Assesment#1 | Assesment#2 | Assesment#3 | Assesment#4 | Assesment#5 | Assesment#6 |
| Mouse ID | CN242 | CN242 | CN242 | CN242 | CN242 | CN242 |
| Gender | Male | Male | Male | Male | Male | Male |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 1 | 1 | 2 | 2 | 2 |
| Limb Tone | 0 | 0 | 0 | 0 | 0 | 0 |
| Weight score | 0 | 0 | 0 | 0 | 0.0 | 0.0 |
| Total Score | 0 | 1 | 1 | 2 | 2 | 2 |
| | | | | | | |
| TCF-Treated | Assesment#1 | Assesment#2 | Assesment#3 | Assesment#4 | Assesment#5 | Assesment#6 |
| Mouse ID | CN243 | CN243 | CN243 | CN243 | CN243 | CN243 |
| Gender | Male | Male | Male | Male | Male | Male |
| Age at assesment | 3 months | 4 months | 5 months | 6 months | 7 months | 8 months |
| Tremor | 0 | 0 | 0 | 0 | 0 | 0 |

FIG. 13 CONITNUED

| | | | | | | |
|---|---|---|---|---|---|---|
| Body position | 0 | 0 | 0 | 0 | 0 | 0 |
| Gait | 0 | 0 | 0 | 0 | 0 | 0 |
| Grooming | 0 | 1 | 1 | 2 | 2 | 2 |
| Limb Tone | 0 | 0 | 0 | 0 | 0 | 0 |
| Weight score | 0 | 0 | 0 | 0 | 0 | 0 |
| Total Score | 0 | 1 | 1 | 2 | 2 | 2 |
| | | | | | | |
| TCF-Treated | Assesment#1 | Assesment#2 | Assesment#3 | Assesment#4 | Assesment#5 | Assesment#6 |
| Mouse ID | CN250 | CN250 | CN250 | CN250 | CN250 | CN250 |
| Gender | Female | Female | Female | Female | Female | Female |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 0 | 1 | 1 | 1 | 1 |
| Limb Tone | 0 | 0 | 0 | 0 | 0 | 0 |
| Weight score | 0 | 0 | 0 | 0 | 0 | 0 |
| Total Score | 0 | 0 | 1 | 1 | 1 | 1 |
| | | | | | | |
| TCF-Treated | Assesment#1 | Assesment#2 | Assesment#3 | Assesment#4 | Assesment#5 | Assesment#6 |
| Mouse ID | CN251 | CN251 | CN251 | CN251 | CN251 | CN251 |
| Gender | Female | Female | Female | Female | Female | Female |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 0 | 1 | 1 | 1 | 1 |
| Limb Tone | 0 | 0 | 0 | 0 | 0 | 0 |
| Weight score | 0 | 0 | 0 | 1 | 0 | 0 |
| Total Score | 0 | 0 | 1 | 2 | 1 | 1 |
| | | | | | | |
| TCF-Treated | Assesment#1 | Assesment#2 | Assesment#3 | Assesment#4 | Assesment#5 | Assesment#6 |
| Mouse ID | CN252 | CN252 | CN252 | CN252 | CN252 | CN252 |
| Gender | Female | Female | Female | Female | Female | Female |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 0 | 1 | 1 | 1 | 1 |
| Limb Tone | 0 | 0 | 0 | 0 | 0 | 0 |
| Weight score | 0 | 0 | 0 | 0 | 1 | 0 |
| Total Score | 0 | 0 | 1 | 1 | 2 | 1 |
| | | | | | | |
| TCF-Treated | Assesment#1 | Assesment#2 | Assesment#3 | Assesment#4 | Assesment#5 | Assesment#6 |
| Mouse ID | CN253 | CN253 | CN253 | CN253 | CN253 | CN253 |
| Gender | Female | Female | Female | Female | Female | Female |

FIG. 13 CONTINUED

| Age at assessment | 3 months | 4 months | 5 months | 6 months | 7 months | 8 months |
|---|---|---|---|---|---|---|
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 0 | 1 | 1 | 1 | 1 |
| Limb Tone | 0 | 0 | 0 | 0 | 0 | 0 |
| Weight score | 0 | 0 | 0 | 0 | 1 | 0 |
| Total Score | 0 | 0 | 1 | 1 | 2 | 1 |
| | | | | | | |
| TCF-Treated | Assesment#1 | Assesment#2 | Assesment#3 | Assesment#4 | Assesment#5 | Assesment#6 |
| Mouse ID | CN254 | CN254 | CN254 | CN254 | CN254 | CN254 |
| Gender | Female | Female | Female | Female | Female | Female |
| Age at assessment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 0 | 1 | 1 | 1 | 1 |
| Limb Tone | 0 | 0 | 0 | 0 | 0 | 0 |
| Weight score | 0 | 0 | 0 | 0 | 1 | 1 |
| Total Score | 0 | 0 | 1 | 1 | 2 | 2 |

| Untreated | Assesment#1 | Assesment#2 | Assesment#3 | Assesment#4 | | |
|---|---|---|---|---|---|---|
| Mouse ID | CN255 | CN255 | CN255 | CN255 | | |
| Gender | Male | Male | Male | Male | | |
| Age at assessment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 1 | 1 | 1 | | |
| Limb Tone | 0 | 0 | 0 | 0 | | |
| Weight score | 0 | 0 | 0 | 0 | | |
| Total Score | 0 | 1 | 1 | 1 | | |
| | | | | | | |
| Untreated | Assesment#1 | Assesment#2 | Assesment#3 | Assesment#4 | | |
| Mouse ID | CN256 | CN256 | CN256 | CN256 | | |
| Gender | Male | Male | Male | Male | | |
| Age at assessment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 1 | 1 | 1 | | |
| Limb Tone | 0 | 0 | 0 | 1 | | |
| Weight score | 0 | 0 | 0 | 0 | | |
| Total Score | 0 | 1 | 1 | 2 | | |
| | | | | | | |
| | Assesment#1 | Assesment#2 | Assesment#3 | Assesment#4 | | |

FIG. 13 CONTINUED

| Mouse ID | CN257 | CN257 | CN257 | CN257 | | |
|---|---|---|---|---|---|---|
| Gender | Male | Male | Male | Male | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 1 | 1 | 1 | | |
| Limb Tone | 0 | 0 | 0 | 1 | | |
| Weight score | 0 | 0 | 0 | 0.0 | | |
| Total Score | 0 | 1 | 1 | 2 | | |
| | | | | | | |
| Untreated | Assesment#1 | Assesment#2 | Assesment#3 | Assesment#4 | | |
| Mouse ID | CN258 | CN258 | CN258 | CN258 | | |
| Gender | Male | Male | Male | Male | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 1 | 1 | 1 | | |
| Limb Tone | 0 | 0 | 0 | 0 | | |
| Weight score | | | 0 | 0 | | |
| Total Score | 0 | 1 | 1 | 1 | | |
| | | | | | | |
| Untreated | Assesment#1 | Assesment#2 | Assesment#3 | Assesment#4 | | |
| Mouse ID | CN259 | CN259 | CN259 | CN259 | | |
| Gender | Male | Male | Male | Male | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 1 | 1 | 1 | | |
| Limb Tone | 0 | 0 | 0 | 1 | | |
| Weight score | 0 | 0 | 0 | 0 | | |
| Total Score | 0 | 1 | 1 | 2 | | |
| | | | | | | |
| Untreated | Assesment#1 | Assesment#2 | Assesment#3 | Assesment#4 | | |
| Mouse ID | CN260 | CN260 | CN260 | CN260 | | |
| Gender | Male | Male | Male | Male | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 1 | 1 | 1 | | |
| Limb Tone | 0 | 0 | 0 | 0 | | |
| Weight score | | 1 | 0 | 0 | | |
| Total Score | 0 | 2 | 1 | 1 | | |
| Total Score | | | | | | |

FIG. 13 CONITNUED

| Untreated | Assesment#1 | Assesment#2 | Assesment#3 | Assesment#4 | | |
|---|---|---|---|---|---|---|
| Mouse ID | CN261 | CN261 | CN261 | CN261 | | |
| Gender | Male | Male | Male | Male | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 1 | 1 | 1 | | |
| Limb Tone | 0 | 0 | 0 | 0 | | |
| Weight score | 2 | 1 | 0 | 0 | | |
| Total Score | 2 | 2 | 1 | 1 | | |
| | | | | | | |
| Untreated | Assesment#1 | Assesment#2 | Assesment#3 | Assesment#4 | | |
| Mouse ID | CN262 | CN262 | CN262 | CN262 | | |
| Gender | Male | Male | Male | Male | | |
| Age at assesment | 3 months | 4 months | 5 months | 6 months | | |
| Tremor | 0 | 0 | 0 | 0 | | |
| Body position | 0 | 0 | 0 | 0 | | |
| Gait | 0 | 0 | 0 | 0 | | |
| Grooming | 0 | 1 | 1 | 1 | | |
| Limb Tone | 0 | 0 | 0 | 0 | | |
| Weight score | 1 | 1 | 0 | 0 | | |
| Total Score | 1 | 2 | 1 | 1 | | |
| | | | | | | |
| Untreated | Assesment#1 | Assesment#2 | Assesment#3 | Assesment#4 | Assesment#5 | Assesment#6 |
| Mouse ID | CN263 | CN263 | CN263 | CN263 | CN263 | CN263 |
| Gender | Male | Male | Male | Male | Male | Male |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 1 | 1 | 1 | 1 | 1 |
| Limb Tone | 0 | 0 | 0 | 0 | 0 | 0 |
| Weight score | 0 | 0 | 0 | 0 | 0 | 0.0 |
| Total Score | 0 | 1 | 1 | 1 | 1 | 1 |
| | | | | | | |
| Untreated | Assesment#1 | Assesment#2 | Assesment#3 | Assesment#4 | Assesment#5 | Assesment#6 |
| Mouse ID | CN264 | CN264 | CN264 | CN264 | CN264 | CN264 |
| Gender | Male | Male | Male | Male | Male | Male |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 1 | 1 | 1 | 1 | 0 |
| Limb Tone | 0 | 0 | 0 | 0 | 0 | 0 |

FIG. 13 CONTINUED

| | | | | | | |
|---|---|---|---|---|---|---|
| Weight score | 0 | 0 | 0 | 0 | 0 | 0 |
| Total Score | 0 | 1 | 1 | 1 | 1 | 0 |
| | | | | | | |
| Untreated | Assesment#1 | Assesment#2 | Assesment#3 | Assesment#4 | Assesment#5 | Assesment#6 |
| Mouse ID | CN265 | CN265 | CN265 | CN265 | CN265 | CN265 |
| Gender | Male | Male | Male | Male | Male | Male |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 1 | 1 | 1 | 1 | 1 |
| Limb Tone | 0 | 0 | 0 | 0 | 0 | 0 |
| Weight score | 0 | 0 | 0 | 0 | 1 | 0 |
| Total Score | 0 | 1 | 1 | 1 | 2 | 1 |
| | | | | | | |
| Untreated | Assesment#1 | Assesment#2 | Assesment#3 | Assesment#4 | Assesment#5 | Assesment#6 |
| Mouse ID | CN266 | CN266 | CN266 | CN266 | CN266 | CN266 |
| Gender | Male | Male | Male | Male | Male | Male |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 1 | 1 | 1 | 1 | 1 |
| Limb Tone | 0 | 0 | 0 | 0 | 0 | 0 |
| Weight score | 0 | 0 | 0 | 0 | 0 | 1 |
| Total Score | 0 | 1 | 1 | 1 | 1 | 2 |
| | | | | | | |
| Untreated | Assesment#1 | Assesment#2 | Assesment#3 | Assesment#4 | Assesment#5 | Assesment#6 |
| Mouse ID | CN267 | CN267 | CN267 | CN267 | CN267 | CN267 |
| Gender | Male | Male | Male | Male | Male | Male |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 1 | 1 | 1 | 1 | 1 |
| Limb Tone | 1 | 0 | 0 | 0 | 0 | 0 |
| Weight score | 1 | 0 | 0 | 0 | 0 | 0 |
| Total Score | 2 | 1 | 1 | 1 | 1 | 1 |
| | | | | | | |
| Untreated | Assesment#1 | Assesment#2 | Assesment#3 | Assesment#4 | Assesment#5 | Assesment#6 |
| Mouse ID | CN268 | CN268 | CN268 | CN268 | CN268 | CN268 |
| Gender | Male | Male | Male | Male | Male | Male |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 1 | 1 | 1 | 1 | 1 |

FIG. 13 CONTINUED

| | | | | | | |
|---|---|---|---|---|---|---|
| Limb Tone | 0 | 1 | 0 | 0 | 0 | 0 |
| Weight score | 0 | 1 | 0 | 0 | 0 | 0 |
| Total Score | 0 | 3 | 1 | 1 | 1 | 1 |
| | | | | | | |
| Untreated | Assesment#1 | Assesment#2 | Assesment#3 | Assesment#4 | Assesment#5 | Assesment#6 |
| Mouse ID | CN269 | CN269 | CN269 | CN269 | CN269 | CN269 |
| Gender | Male | Male | Male | Male | Male | Male |
| Age at assesment | 3 months | 4 months | 5 months | 6 months | 7 months | 8 months |
| Tremor | 0 | 0 | 0 | 0 | 0 | 0 |
| Body position | 0 | 0 | 0 | 0 | 0 | 0 |
| Gait | 0 | 0 | 0 | 0 | 0 | 0 |
| Grooming | 0 | 1 | 1 | 1 | 1 | 1 |
| Limb Tone | 0 | 0 | 0 | 0 | 0 | 0 |
| Weight score | 0 | 0 | 0 | 0 | 0 | 0 |
| Total Score | 0 | 1 | 1 | 1 | 1 | 1 |

TRIPLE COMBINATION FORMULATION FOR TREATMENT OF CHRONIC PAIN

CROSS-REFERENCE TO RELATED APPLICATIONS

This application claims priority to U.S. Provisional Application No. 62/594,216, filed Dec. 4, 2017, which is incorporated herein in its entirety.

STATEMENT REGARDING FEDERALLY SPONSORED RESEARCH

This invention was made with government support under DE022746 and NS035115 awarded by the National Institutes of Health. The government has certain rights in the invention.

BACKGROUND OF THE INVENTION

The field of the invention is related to therapeutics and methods of treating chronic pain.

Chronic pain affects at least 100 million American adults—more than the total affected by heart disease, cancer, and diabetes combined. Chronic pain remains the number one source of disability in the US and 5th worldwide. Pain also costs the nation around $500 billion each year in medical treatment and lost productivity. Every new epidemiological study indicates that these rates continue to increase worldwide. Treatment options for chronic pain remain limited. The majority of chronic pain patients are not satisfied with their pain management, as pain relief is short in duration, associated with adverse effects, and the most effective options, namely opioids, are linked to addiction and related mortality[5] at an epidemic rate[6]. Thus, novel, non-opioidergic treatment options are urgently needed for chronic and especially for neuropathic pain conditions.

There is a need for new therapeutic formulations for treatment of chronic pain.

SUMMARY OF THE INVENTION

The present invention overcomes the aforementioned drawbacks by providing formulations and methods of treating chronic pain.

In one aspect, the disclosure provides triple combination formulations for the use in the treatment and management of chronic pain.

In one aspect, the disclosure provides a method of treating chronic pain in a subject in need thereof, the method comprising administering to the subject a composition comprising (i) a histone deacetylase (HDAC) inhibitor, (ii) a cyclodextrin or salt thereof, and (iii) polyethylene glycol (PEG) or propylene glycol, wherein the composition is provided in a therapeutically effective amount to treat the chronic pain. In one aspect, the HDAC inhibitor is vorinostat. In one aspect, the cyclodextrin is 2-hydroxypropyl-b-cyclodextrin (HPBCD). In one aspect, the polyethylene glycol (PEG) or propylene glycol is polyethylene glycol. In one further aspect, the composition comprises, consists of or consists essentially of vorinostat as the HDACi, 2-hydroxypropyl-b-cyclodextrin (HPBCD) as the cyclodextrin, and polyethylene glycol.

In another aspect, the present disclosure provides a method of reducing or inhibiting one or more symptoms of chronic pain, the method comprising administering to the subject a composition comprising (i) a histone deacetylase (HDAC) inhibitor, (ii) a cyclodextrin or salt thereof, and (iii) polyethylene glycol (PEG) or propylene glycol, wherein the composition is provided in a therapeutically effective amount to reduce or inhibit one or more symptom of chronic pain. In one aspect, the HDAC inhibitor is vorinostat. In one aspect, the cyclodextrin is 2-hydroxypropyl-b-cyclodextrin (HPBCD). In one aspect, the polyethylene glycol (PEG) or propylene glycol is polyethylene glycol. In one further aspect, the composition comprises, consists of or consists essentially of vorinostat as the HDACi, 2-hydroxypropyl-b-cyclodextrin (HPBCD) as the cyclodextrin, and polyethylene glycol.

In another aspect, the disclosure provides a use of a composition comprising (i) a histone deacetylase (HDAC) inhibitor, (ii) a cyclodextrin or salt thereof, and (iii) polyethylene glycol (PEG) or propylene glycol for manufacture of a medicament for the treatment of chronic pain or inhibition of symptoms of chronic pain.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 7C) Bar diagram is quantification of Purkinje neurons from same number of mice. Two sections per mouse were analyzed for counting. Numbers (mean±SD) are relative to untreated healthy mice. Un, untreated; Tr, treated.

(FIG. 8A) Histological analysis using H&E staining. (FIG. 8B) Analysis of neuroinflammation in long-term TCF-treated mice. Fluorescence microscopy detection of activated microglial cells (green, white arrows) with anti Iba-1 antibodies in the hippocampus (from the regions indicated) from untreated and TCF-treated healthy (Npc1$^{+/nmf164}$). The images shown are representative from two untreated (age 108 and 109 days) and four TCF-treated (age 225-265 days) healthy mice. (FIG. 8C) Bar diagram is quantification of microglial cells from same number of mice. Two sections per mouse were studied. Scale bar, 25 μm (FIG. 9A) Major neurobehavioral symptoms and (corresponding human disease domain) as follows: tremor (motor); gait (ambulation); grooming (cognition); body position (cognition and motor); limb tone (motor) and weight loss (dysphagia) were assessed on a scale of 0-2 except weight loss assessed as 0-3. The cumulative score is shown at indicated time points. Score of 3 or below is baseline. For 3-6 months (mo) untreated, n=15 (all males) and treated, n=17 (7 males and 10 females). For 7 and 8 months untreated, n=7 (all males) and treated, n=9 (4 males and 5 females), (FIG. 9B) Weight of mice in FIG. 9A. Data are mean±SD. See also FIG. 13.

FIG. 13 shows assessment data for TCF-treated and untreated mice.

DETAILED DESCRIPTION

Figure 1:
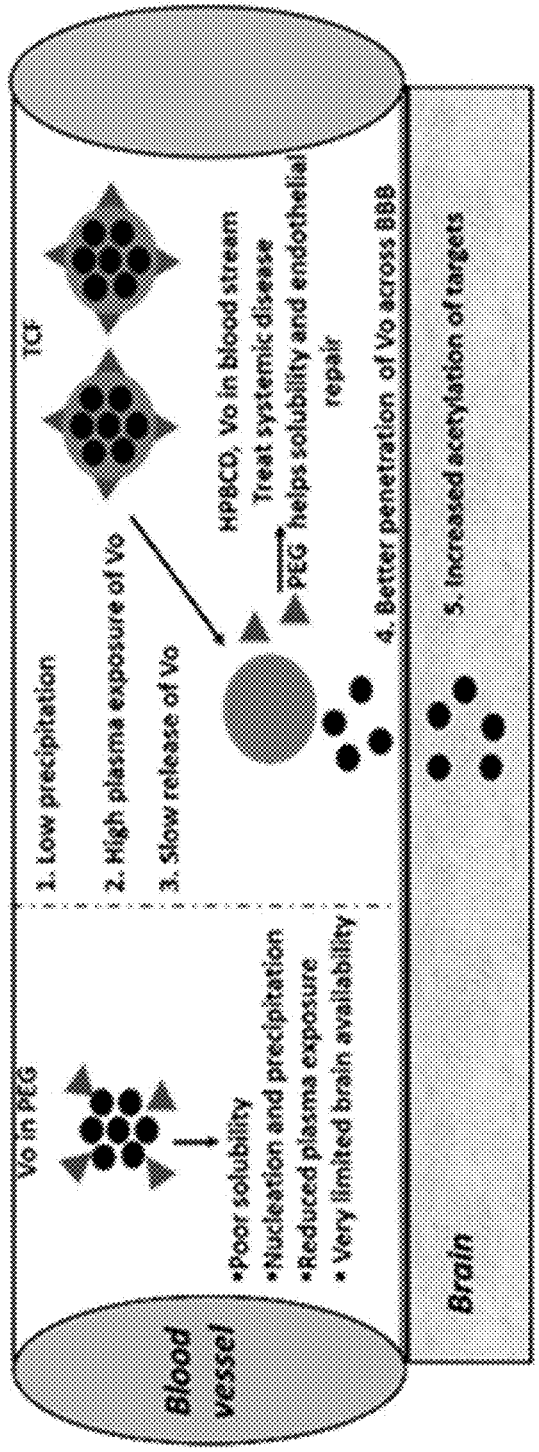
FIG. 1 depicts the working model of action for the triple combination formulation (TCF), adapted from US 2015/0359762, incorporated by reference in its entirety.

Embodiments of the present disclosure provide methods of treating and managing chronic pain. The methods comprise a new drug formulation comprising a triple combination formulation (TCF). The TCF comprises, consists essentially of, or consists of, a histone deacetylase (HDAC), a cyclodextrin and polyethylene glycol (PEG) or propylene glycol in a therapeutically effective amount to treat, inhibit, ameliorate, delay or reduce at least one symptom of chronic pain in a subject. In a preferred embodiment, the composition comprises, consists essentially of, or consists of, the TCF where the HDAC may be vorinostat (Vo, a pan-HDACi), the cyclodextrin may be 2-hydroxypropyl-b-cyclodextrin (HPBCD), and polyethylene glycol or propylene glycol may be polyethylglycol.

Histone deacetylase inhibitors (HDACi) are an important class of emerging therapeutics approved for treating rare cancers. They elicit complex cellular responses by blocking HDAC enzymes. In selected genetic disorders, HDACi induce desired transcriptional expression of genes (through histone acetylation) as well as confer indirect benefits through acetylation of non-histone proteins (such as transcription factors and heat shock proteins) that modulate chaperones and proteostatic networks. However, despite recognition that epigenetic mechanisms are important for brain function, treatment of brain-dependent diseases requires effective HDACi penetration across the blood-brain barrier (BBB). But at the same time, chronic inhibition of HDAC function in the brain is deleterious. For example, histone deacetylase 3 (HDAC3) is essential for Purkinje cell function and therefore cannot be continuously antagonized, but rather HDACi dosing must be kept low and include rest periods.

Epigenetic mechanisms and histone acetylation and deacetylation have been studied in animal pain models, examining peripheral, spinal cord, and cortical mechanisms. Early studies with systemically applied HDACi show confusing results. However, intrathecal injection of pan-HDACi baicalin reverses pain behavior and reduces histone acetylation in SNI. Systemically applied valproic acid and curcumin (HDACi-s) also show modest analgesia. In an inflammatory pain model, intrathecal HDACs, vorinostat, trichostatin A (TSA), or dacinostat (LAQ824) reduced hyperalgesia and enhanced histone acetylation in the spinal cord dorsal horn. The inventor's prior studies point to brain limbic circuitry playing a critical role in risk for chronic pain and in adaptations that accompany the transition into a chronic pain state. These and other studies imply that brain circuits involved in learning, motivation, and mood regulation all participate in the development of chronic pain and may be targets of epigenetic changes which in turn would exert top-down regulation of nociceptive circuits. Recent evidence shows brainstem histone H3 acetylation, and prefrontal cortex (PFC) and amygdala DNA methylation in various animal pain models, some of which correlate with the pain behavior. Epigenetic chronic pain-induced modifications have also been observed in brain reward circuitry (accumbens), and HDACi infused directly in the amygdala also reduces chronic pain-like behavior. However, the ability to deliver HDACi across the blood brain barrier has been limited.

This disclosure describes the use of a novel TCF that is able to cross the blood brain barrier and to treat chronic pain. Suitable formulations of the TCF are disclosed herein in Example 2, in Alam et al, 2017, bioRxiv (doi: doi.org/10.1101/191635)) and in Alam, M. S., Getz, M. & Haldar, K. Chronic administration of an HDAC inhibitor treats both neurological and systemic Niemann-Pick type C disease in a mouse model. Science translational medicine 8, 326ra323, doi:10.1126/scitranslmed.aad9407 (2016), each of which are incorporated by reference in their entirety.

For purposes of the present invention, "treating" or "treatment" describes the management and care of a subject for the purpose of combating the disease, condition, or disorder. Treating includes the administration of an inhibitor of embodiments of the present disclosure to prevent the onset of the symptoms or complications, alleviating the symptoms or complications, or eliminating the disease, condition, or disorder. Treating also encompasses therapeutic and palliative treatment. The aim of treatment includes the alleviation or prevention of symptoms, slowing or stopping the progression or worsening of a disease, disorder, or condition and/or the remission of the disease, disorder or condition. The term "treat," "treating" or "treatment" of a chronic pain encompasses, but is not limited to, reducing, inhibiting, alleviating, improving, delaying or limiting at least one symptom of chronic pain or any aspect of chronic pain. For purposes of this disclosure, beneficial or desired clinical results include, but are not limited to, one or more of the following: including lessening severity, alleviation of pain and/or a symptom associated with chronic pain.

The term "effective amount" or "therapeutically effective amount" refer to an amount sufficient to effect beneficial or desirable biological and/or clinical results. In one embodiment, the "effective amount" is an amount sufficient to reduce, inhibit, alleviate or improve one or more symptom associated with chronic pain. An "effective treatment" refers to treatment producing a beneficial effect, e.g., amelioration of at least one symptom of chronic pain. A beneficial effect can take the form of an improvement over baseline, i.e., an improvement over a measurement or observation made prior to initiation of therapy according to the method. A beneficial effect can also take the form of reducing, inhibiting or preventing at least one symptom of chronic pain, e.g. lessening the severity of the pain, alleviating the pain or lessening or alleviating at least one symptom associated with chronic pain.

Reducing chronic pain and/or symptoms associated with chronic pain means any of reducing severity (which can include reducing need for and/or amount (e.g. exposure to) other drugs and/or therapies generally used for pain), duration and/or frequency. Ameliorating chronic pain and/or a symptom associated with chronic pain means a lessening or improvement of one or more symptoms of chronic pain and/or symptoms associated with chronic pain as compared to not administering the TCF. Ameliorating also includes shortening or reducing a duration of a symptom.

As used herein, "delaying" the development of chronic pain means to defer, hinder, slow, retard, stabilize, and/or postpone progression of chronic pain and/or a symptom associated with chronic pain. This delay can be of varying lengths of time, depending on the history of the disease and/or individuals being treated. As is evident to one skilled in the art, a sufficient or significant delay can, in effect, encompass prevention, in that the individual does not develop chronic pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

The term "pharmaceutically acceptable carrier" refers any carrier, diluent, or excipient that is compatible with other ingredients of the formulation and not deleterious to the recipient. A pharmaceutically acceptable carrier can be selected on the basis of the selected route of administration and standard pharmaceutical practice. The TCF may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, but are not limited to, for example, solutions, parenteral solutions, injectable solutions, troches, solid preparations, suppositories, or suspensions.

In an embodiment, the TCF is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

For oral administration, the active agent may be combined with one or more inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents, or lubricating agents.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, intraaural administration, intracerebral administration, rectal administration, sublingual administration, buccal administration, and parenteral administration, including injectable such as intravenous administration, intra-arterial administration, intramuscular administration, intradermal administration, intrathecal administration and subcutaneous administration. Administration can be continuous or intermittent. In various aspects, a preparation can be administered therapeutically; that is, administered to treat an existing disease or condition. In a preferred embodiment, the compounds or compositions are administered by intravenous, oral, transdermal, or inhalation. In one embodiment, the compounds or compositions are administered intraperitoneally as an injection. In another embodiment, the compounds or compositions are administered subcutaneously.

The terms "subject" and "patient" are used interchangeably and refer to any animal (e.g., a mammal), including, but not limited to, humans, non-human primates, rodents, and the like, which is to be the recipient of a particular treatment. Typically, the terms "subject" and "patient" are used interchangeably herein in reference to a human subject. In a preferred embodiment, the subject is a human having chronic pain.

According to a preferred embodiment of the present disclosure the chronic pain comprises one or more of chronic nociceptive pain, chronic neuropathic pain, chronic inflammatory pain, arthritis pain, fibromyalgia, breakthrough pain, persistent pain, hyperalgesia, allodynia, central sensitization, peripheral sensitization, disinhibition and augmented facilitation and cancer pain. In some embodiments, the chronic pain is cancer pain, preferably cancer pain arising from malignancy or from cancer preferably selected from one or more of: adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, lymphoma, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, bone cancer, sarcomas cancer of the connective tissue, cancer of bone tissue, cancer of blood-forming cells, cancer of bone marrow, multiple myeloma, leukemia, primary or secondary bone cancer, tumors that metastasize to the bone, tumors infiltrating the nerve and hollow viscus, tumors near neural structures. Further preferably the cancer pain comprises visceral pain, preferably visceral pain which arises from pancreatic cancer and/or metastases in the abdomen. Further preferably the cancer pain comprises somatic pain, preferably somatic pain due to one or more of: bone cancer, metastasis in the bone, postsurgical pain, sarcomas cancer of the connective tissue, cancer of bone tissue, cancer of blood-forming cells of the bone marrow, multiple myeloma, leukemia, primary or secondary bone cancer.

The composition may be administered as a single dose, or the composition components may be administered separately. For example, in some embodiments, HDAC may be administered separately from the cyclodextrin and polypropylene glycol or propylene glycol. In some embodiments, the method includes administering HDAC before or after administering the cyclodextrin and polyethylene glycol or polypropylene glycol. In some embodiments, the method includes administering cyclodextrin before administering the remaining components. In some embodiments, the method includes administering the HDAC separately. Preferably, however, the composition is administered as a single admixture.

The TCF may be administered simultaneously/concurrently or sequentially. Simultaneous administration will include the administration of the components of the composition administered in different formulations, taken separately but within an hour of administration of the first component (e.g., seconds or minutes in-between). Suitably, when administered sequentially, for example, the HDAC may be administered first followed by administration of the cycodextrin and PEG. The time between the administration of the different components can be adjusted for maximum efficacy, and may be in the order of minutes or hours or longer.

Administering may occur by different timings, for example once or more than once. In some embodiments, the administering is carried out periodically or substantially periodically, for example, daily, weekly, monthly, a multiple thereof, a fraction thereof, or a combination thereof. In some embodiments, the administering is carried out daily, a multiple thereof, a fraction thereof, or a combination thereof. In some embodiments, the administering is carried out weekly, a multiple thereof, a fraction thereof, or a combination thereof. In some embodiments, the administration may occur regularly, e.g., every week throughout the duration of treatment, or it may occur irregularly, e.g., once a week for a few weeks, then twice a week or not at all for a few weeks, etc. Similarly, in some embodiments, a rest period of non-administration may occur between administrations. The rest period may occur regularly or irregularly.

In another embodiment, the disclosure provides a method of reducing or inhibition one or more symptoms of chronic pain, the method comprising administering to the subject a composition comprising a (i) histone deacetylase (HDAC) inhibitor, (ii) a cyclodextrin or salt thereof, and (iii) polyethylene glycol (PEG) or propylene glycol, wherein the composition is provided in a therapeutically effective amount to reduce or inhibit one or more symptom of chronic pain.

The present disclosure also provides use of a composition comprising a (i) histone deacetylase (HDAC) inhibitor, (ii) a cyclodextrin or salt thereof, and (iii) polyethylene glycol (PEG) or propylene glycol for manufacture of a medicament for the treatment of chronic pain or inhibition of symptoms of chronic pain. In some embodiments, the medicament is prepared to be administered orally, sublingually, vial inhalation, transdermally, subcutaneously, intravenously, intra-arterially, intra-articulary, peri-articularly, locally or intra-muscularly. In some embodiments, the HDAC inhibitor may be vorinostat, the cyclodextrin may be 2-hydroxypropyl-b-cyclodextrin (HPBCD) and the polyethylene glycol (PEG) or propylene glycol is polyethylene glycol.

As stated above, suitable formulations of the TCF are disclosed herein in Example 2, in Alam et al, 2017, bioRxiv (doi: doi.org/10.1101/191635), and in Alam, M. S., Getz, M. & Haldar, K. Chronic administration of an HDAC inhibitor treats both neurological and systemic Niemann-Pick type C disease in a mouse model. *Science translational medicine* 8, 326ra323, doi:10.1126/scitranslmed.aad9407 (2016), the contents of which are incorporated by reference in its entirety. Suitable formulations of the TCF described therein can be used in the methods described herein.

The dosage amount of the HDACi is an amount ranging from about 0.1 to about 500 mg/kg. This range includes all values and subranges therebetween, including 0.1, 0.5, 1, 5, 10, 15, 20, 25, 30, 35, 40, 45, 50, 55, 60, 65, 70, 75, 80, 85, 90, 95, 100, 150, 200, 250, 300, 350, 400, 450, 500 mg/kg, or any combination thereof. In some embodiments, the dosage amount is based on a 50 mg/kg murine dose, and may be scaled for human treatment, as is known. For example, a 50 mg/kg murine dose may scale to 150 mg/m$^2$ in children. Such scaling is well within the skill of the artisan and may be suitably applied to any dosage for any compound or compounds herein.

The HDAC inhibitor (HDACi) used in the present compositions include, but are not limited to, for example, hydroxamic acids, aliphatic acids, hydroxamates, benzamides, thiophene benzamide, butyrates, sodium butyrate, phenylbutyrate, cyclic tetrapeptide, trapoxin B, depsipeptide, cyclic peptide, electrophilic ketones, dacinostat/LAQ-824, NVP-LAQ824, givinostat/ITF-2357, bufexamac, pyroxamide, sulforaphane, trichostatin A (TSA) and analogs thereof, miglustat/OGT-918, SAHA/vorinostat/MK-0683/Zolinza, entinostat/MS-275, panobinostat/LBH-589, droxinostat/CMH, quisinostat/JNJ-26481585, PCI-24781/CRA-024781, romidepsin/FK228/FR901228/NSC 630176/depsipeptide, valproic acid, PCI-34051, CI-994/tacedinaline, M-344, rocilinostat/ACY-1215, apicidin, R-306465, mocetinostat/MGCD-0103, belinostat/PXD-101, chidamide/CS-055, abexinostat/PCI-24781, SB-939, resminostat/45C-201, kevetrin, CUDC-101, AR-42, CHR-2845, CHR-3996, 4SC-202, CG-200745, ACY-1215, ME-344, RGFP-136, CBHA, AN-9, or any combination thereof. In a preferred embodiment, the HDACi is vorinostat (Vo). In some embodiments, the use of two or more HDACi's is possible.

The cyclodextrin used in the present TCF compositions include, but are not limited to, for example, hydroxypropyl-β-cyclodextrin, 2-hydroxypropyl-β-cyclodextrin, dimethyl-β-cyclodextrin, hydroxypropyl-α-cyclodextrin, hydropropyl-γ-cyclodextrin, or any combination thereof. In a preferred embodiment, the cyclodextrin is hydroxypropyl-β-cyclodextrin, preferably 2-hydroxypropyl-β-cyclodextrin (HPBCD). The cyclodextrin may have any average molecular weight ranging, for example from about 970 to about 6,000 Da depending, for example, on the type of cyclodextrin (α, β, or γ) and whether it is crosslinked or uncrosslinked, substituted or unsubstituted, the degree of substitution, and the like, as is known in the art. In some embodiments, the cyclodextrin is 2-hydroxypropyl-β-cyclodextrin and may have an average molecular weight of 1396 Da. In some embodiments, two or more cyclodextrins may be used.

In some embodiments, the cyclodextrin may be administered in an amount ranging from about 1000 to about 40,000 mg/kg. This range includes all values and subranges therebetween, including 1000, 1200, 1400, 1600, 1800, 2000, 2100, 2200, 2300, 2400, 2500, 2600, 2700, 2800, 2900, 3000, 3500, 4000, 5000, 6000, 7000, 8000, 9000, 10,000, 20,000, 30,000, 40,000 mg/kg, or any combination thereof. In some embodiments, the dosage amount is based on a 2000 mg/kg murine dose, and may be scaled for human treatment, as is known.

The polyethylene glycol and propylene glycol are not particularly limiting. In some embodiments, polyethylene glycol is used.

The molecular weight of the polyethylene glycol or polypropylene glycol is not particularly limiting. In some embodiments, the average molecular weight may range from about 100 to about 6000 Da. This range includes all values and subranges therebetween, including 100, 200, 300, 400, 500, 600, 700, 800, 900, 1000, 1200, 1400, 1600, 1800, 2000, 2100, 2200, 2300, 2400, 2500, 2600, 2700, 2800, 2900, 3000, 3500, 4000, 5000, 6000 Da, or any combination thereof.

In some embodiments, polyethylene glycol is used, and the average molecular weight may range from about 100 to about 6000 Da. This range includes all values and subranges there between, including 100, 200, 300, 400, 500, 600, 700, 800, 900, 1000, 1200, 1400, 1600, 1800, 2000, 2100, 2200, 2300, 2400, 2500, 2600, 2700, 2800, 2900, 3000, 3500, 4000, 5000, 6000 Da, or any combination thereof.

In some embodiments, polyethylene glycol having an average molecular weight of 100-1000 Da is used. In some embodiments, polyethylene glycol having an average molecular weight of 200-600 is used. In some embodiments, polyethylene glycol having an average molecular weight of 400 is used. In a preferred embodiment, the polyethylene glycol 400 is used. Mixtures of polyethylene glycols having different molecular weights are possible.

The amount of polyethylene glycol is not particularly limiting. In some embodiments, the amount of polyethylene glycol may suitably range from about 1 to about 80% of the composition by weight. This range includes all values and subranges there between, including 1, 2, 3, 4, 5, 6, 7, 8, 9, 10, 15, 20, 25, 30, 35, 40, 45, 50, 55, 60, 65, 70, 75, 80%, or any combination thereof, based on the weight of the composition. In a preferred embodiment, PEG is used in an amount of 40-60% by weight of the composition, for example, 45%.

The relative amounts of HDACi:cyclodextrin:polyethylene glycol or propylene glycol are not particularly limiting. In some embodiments, the HDACi:cyclodextrin:polyethylene glycol or propylene glycol molar ratio may be about 1-100:1-1000:1-1000. In some embodiments, the HDACi:cyclodextrin:polyethylene glycol or propylene glycol molar ratio may be about 1-100:1-100:1-1000. In some embodiments, the composition has a HDACi:polyethylene glycol molar ratio of about 1-10:1-1000:1-1000. In some embodiments, the composition has a HDACi:cyclodextrin:polyethylene glycol molar ratio of about 1-10:1-100:1-1000. In some embodiments, the composition has a HDACi:cyclodextrin:polyethylene glycol molar ratio of about 1:1-100:1-500. In some embodiments, the composition has a HDACi:cyclodextrin:polyethylene glycol molar ratio of about 1:1-10:1-100. In some embodiments, the composition has a HDACi:cyclodextrin:polyethylene glycol molar ratio of about 1:5-100:10-100. In some embodiments, the composition has a HDACi:cyclodextrin:polyethylene glycol molar ratio of about 1:5-10:10-100. In some embodiments, the composition includes HDACi, cyclodextrin, and polyethylene glycol in a HDACi:cyclodextrin:polyethylene glycol molar ratio of about 1-100:1-1000:1-1000. In some embodiments, the composition includes HDACi, cyclodextrin, and polyethylene glycol in a HDACi:cyclodextrin:polyethylene glycol molar ratio of about 1-100:1-100:1-1000. Each of these ranges independently includes all values and subranges therebetween.

For example, the 1-100 range given independently includes all values and subranges therebetween, including 1, 2, 3, 4, 5, 6, 7, 8, 9, 10, 15, 20, 25, 30, 35, 40, 45, 50, 55, 60, 65, 70, 75, 80, 85, 90, 95, 100, or any combination thereof. Similarly, the 1-1000 range given for the cyclodextrin independently includes all values and subranges therebetween, including 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or any combination thereof. Likewise, the 1-1000 range given independently includes all values and subranges therebetween, including 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or any combination thereof.

The molar ratio of HDACi:cyclodextrin is not particularly limiting, and may suitably range from 0.001 to 100. This range includes all values and subranges therebetween, including 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or any combination thereof.

Similarly, the molar ratio of HDACi:polyethylene glycol is not particularly limiting, and may suitably range from 0.001 to 100. This range includes all values and subranges therebetween, including 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or any combination thereof.

In some embodiments, the composition has a HDACi:cyclodextrin molar ratio of less than about 0.2, ≤0.13, less than about 0.13, 0.001 to less than about 0.2, 0.001 to ≤0.13, 0.001 to less than about 0.13, 0.01 to about 0.15, 0.01 to ≤0.13, 0.01 to less than about 0.13, 0.01 to ≤0.1, 0.01 to less than about 0.1, 0.01 to ≤0.065, 0.01 to less than about 0.065, about 0.13, or about 0.065 as appropriate.

In some embodiments, the composition has a HDACi:cyclodextrin molar ratio of less than about 0.2, ≤0.13, less than about 0.13, 0.001 to less than about 0.2, 0.001 to ≤0.13, 0.001 to less than about 0.13, 0.01 to 0.15, 0.01 to ≤0.13, 0.01 to less than about 0.13, 0.01 to ≤0.1, 0.01 to less than about 0.1, 0.01 to ≤0.065, 0.01 to less than about 0.065, about 0.13, or about 0.065 as appropriate.

In some embodiments, the composition has a vorinostat:2-hydroxypropyl-β-cyclodextrin molar ratio of less than about 0.2, ≤0.13, less than about 0.13, 0.001 to less than about 0.2, 0.001 to ≤0.13, 0.001 to less than about 0.13, 0.01 to 0.15, 0.01 to ≤0.13, 0.01 to less than about 0.13, 0.01 to ≤0.1, 0.01 to less than about 0.1, 0.01 to ≤0.065, 0.01 to less than about 0.065, about 0.13, or about 0.065 as appropriate.

In some embodiments, the composition has a HDACi:polyethylene glycol or propylene glycol molar ratio of less than 1, 0.9, 0.8, 0.7, 0.6, 0.5, 0.4, 0.3, 0.2, 0.15, 0.1, 0.09, 0.08, 0.07, 0.06, 0.05, 0.04, 0.03, 0.02, 0.15, 0.01, or any combination thereof.

In some embodiments, the composition has a HDACi:polyethylene glycol molar ratio of less than 1, 0.9, 0.8, 0.7, 0.6, 0.5, 0.4, 0.3, 0.2, 0.15, 0.1, 0.09, 0.08, 0.07, 0.06, 0.05, 0.04, 0.03, 0.02, 0.15, 0.01, or any combination thereof.

In some embodiments, the composition has a HDACi:polyethylene glycol 400 molar ratio of less than 1, 0.9, 0.8, 0.7, 0.6, 0.5, 0.4, 0.3, 0.2, 0.15, 0.1, 0.09, 0.08, 0.07, 0.06, 0.05, 0.04, 0.03, 0.02, 0.15, 0.01, or any combination thereof.

In some embodiments, the composition has a vorinostat:polyethylene glycol 400 molar ratio of less than 1, 0.9, 0.8, 0.7, 0.6, 0.5, 0.4, 0.3, 0.2, 0.15, 0.1, 0.09, 0.08, 0.07, 0.06, 0.05, 0.04, 0.03, 0.02, 0.15, 0.01, or any combination thereof.

The composition may or may not contain DMSO. In some embodiments, the composition does not contain DMSO.

In some embodiments, kits for carrying out the methods described herein are provided. The kits provided may contain the necessary components with which to carry out one or more of the above-noted methods. In one embodiment, a kit for treating chronic pain. The kit may comprise at least one composition of the present invention and instructions for use.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim.

The present disclosure has been described in terms of one or more preferred embodiments, and it should be appreciated that many equivalents, alternatives, variations, and modifications, aside from those expressly stated, are possible and within the scope of the disclosure.

The disclosure will be more fully understood upon consideration of the following non-limiting examples.

EXAMPLES

Example 1: TCF Use in Treatment of Chronic Pain

A new drug formulation comprising a triple combination formulation (TCF) comprising Vo (a pan-HDACi), the caging agent 2-hydroxypropyl-b-cyclodextrin (HPBCD), and polyethylene glycol (PEG) (FIG. 1) was formulated as a therapeutic for neurodegenerative disorders, and shows efficacy in a mouse model of Niemann-Pick type C disease. TCF boosts the ability of HDACi to cross the blood brain barrier. In the mouse, intraperitoneal (ip) TCF increases histone acetylation in the brain, and low-dose repeated TCF treatment in $Npc1^{nmf164}-/-$ mice increases Npc1 transcript and protein levels in the brain, and extends animal survival by 100% (See Alam et al, 2017, bioRxiv (doi: doi.org/10.1101/191635, incorporated by reference). Importantly, even after 8-12 months of once-weekly ip TCF, normal mice showed no detectable toxicity (See Alam, M. S., Getz, M. &

Haldar, K. Chronic administration of an HDAC inhibitor treats both neurological and systemic Niemann-Pick type C disease in a mouse model. *Science translational medicine* 8, 326ra323, doi:10.1126/scitranslmed.aad9407 (2016), incorporated by reference in its entirety.

The Example shows that ip TCF in rats with spared nerve injury (SNI; a validated rodent model for human chronic pain) decreases the primary neuropathic pain-related behavior, tactile allodynia, by 50% for a duration of about 30 days. This analgesia seems quite specific as TCF did not interfere with tactile sensitivity of the uninjured paw, and pain relief was not accompanied with motor or anxiety-like deficits. The sustained long-duration and large magnitude of pain relief with TCF is itself very exciting as no other clinically available pain pharmacotherapy shows such properties.

Our data in the SNI rat and one-year TCF-treated mice demonstrate they do not exhibit obvious signs of toxicity.

Medicinal chemistry approaches have attempted to develop brain permeant and selective HDACi (and KDACi). But the path of new chemical entities to the clinic is long (and to date none have yet been chronically administered). In contrast the TCF boosts brain penetration of a FDA approved Vo delivered with GRAS (generally regarded as safe) compounds HPBCD and PEG, which are also well tolerated. While brain concentrations of Vo achieved confer substantial neurological benefit in mice, they are low (which could indeed explain the observed tolerance). For multiple years, the inventors have been testing various chemical formulations as potential therapies for chronic pain. The ability of this novel TCF formulation rendering the HDACi vorinostat (Vo) to cross the BBB but with no detectable metabolic toxicity has been surprisingly found to be able to also control chronic neuropathic pain. This Example demonstrates pain relief and for providing a tool with exciting potential to explore sustained central epigenetic control of chronic pain.

Simultaneously increasing BBB permeation to functional CNS-active levels and repeated administration of Vo via the TCF without toxicity achieves long awaited milestones in the utilization of an HDACi in the treatment of brain epigenetically modulated disease conditions, such as chronic pain.

Figures 2A, 2B:
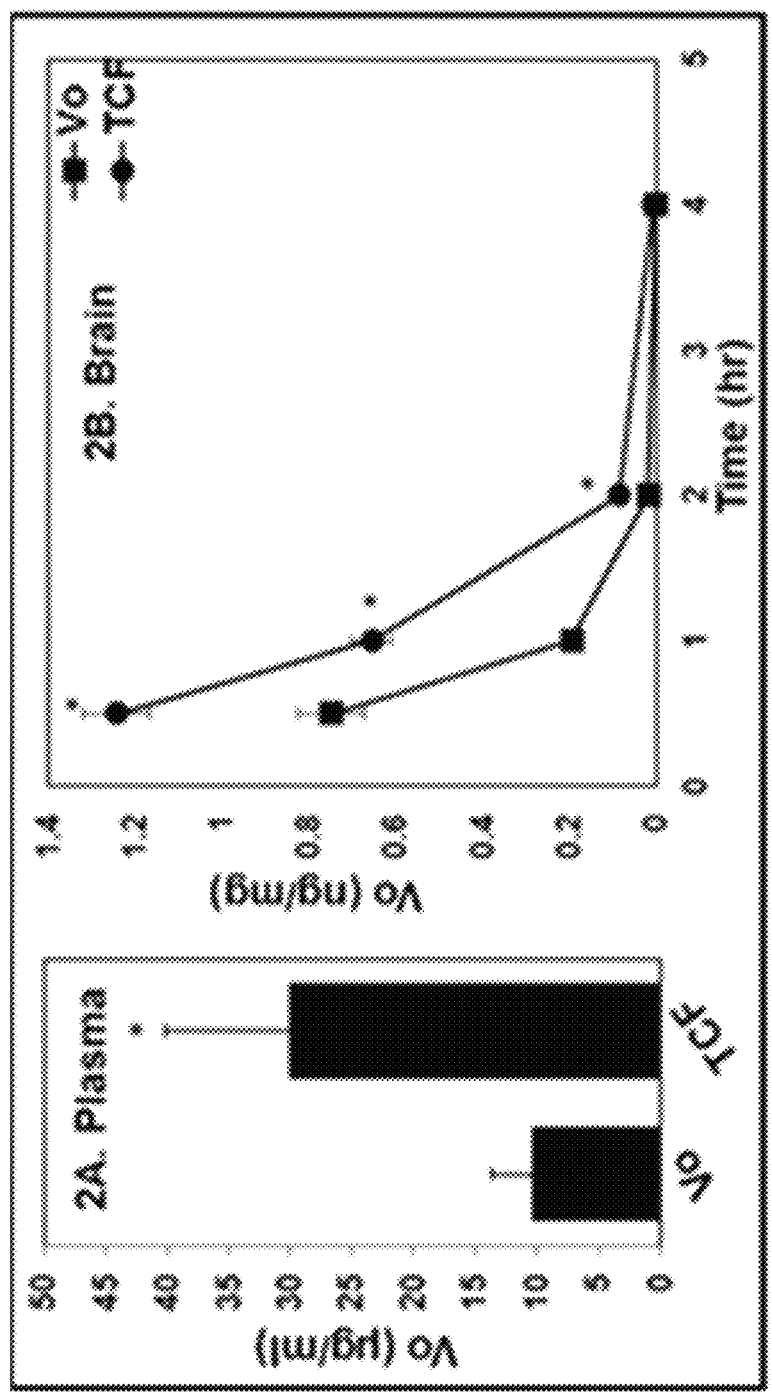
FIGS. 2A-2B depict the increased plasma and brain concentration of vorinostat (Vo) in TCF injected mice. A. Plasma. $Npc1^{+/nmf164}$ injected i.p. with Vo or TCF. Blood at 1 h post injection. Mean±SEM from two independent experiments shown (5 mice/group, each experiment). *p<0.05, TCF vs Vo. B. Pharmacokinetics of Vo in mouse brain. $Npc1^{+/nmf164}$ mice injected i.p. with Vo or TCF. At indicated times, animals sacrificed, perfused with PBS and brain was harvested. n=10 mice at 0.5 h; n=5 remaining time points. *p<0.05. Vo conc. determined by mass spec. Alam et al.[1]
Figures 3A, 3B:
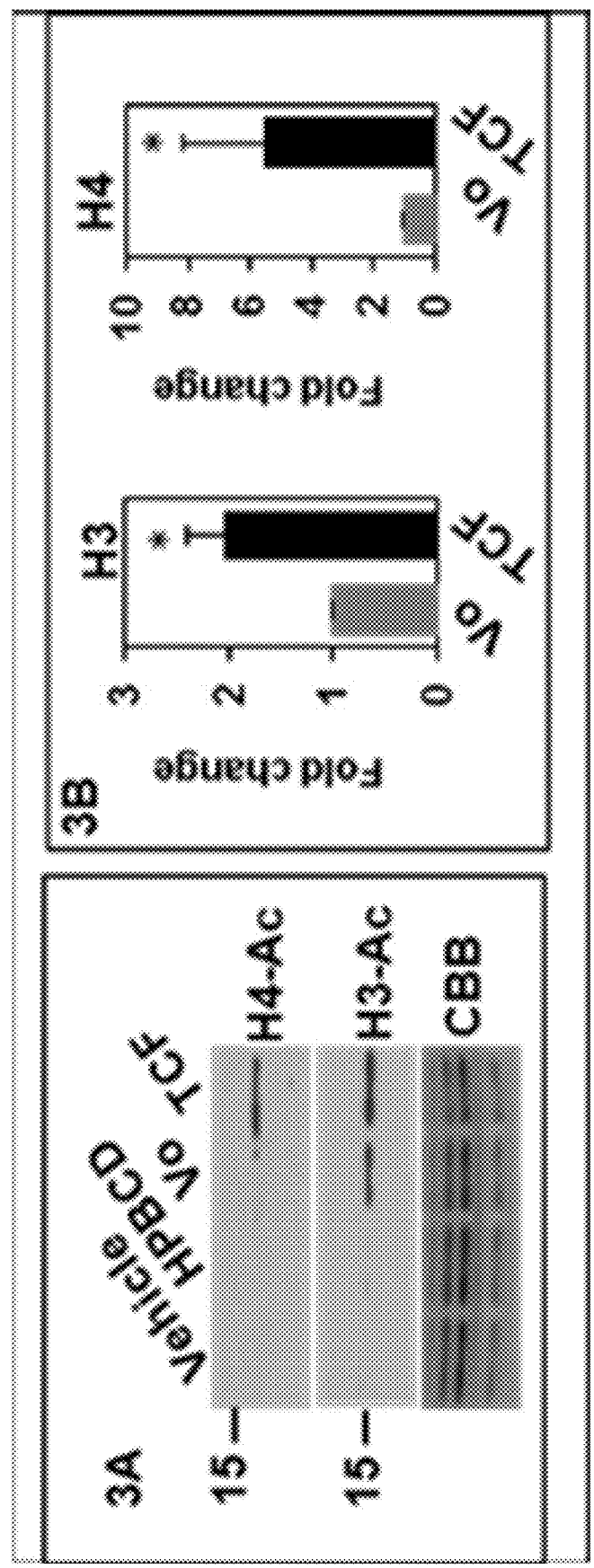
FIGS. 3A-3B show acetylation of histone 3 and 4 in brain of $Npc1^{nmf164}$ mice. A. Western blots show acetylation of histones 3 and 4 (H3 and H4) in brain of $Npc1^{nmf164}$ mice at 60 min after administration of TCF, its components or vehicle control. n=3 (3 mice in each n). Coomassie stained gel (CBB; blue) confirmed equal sample loading. B. Quantitation of A. Fold change relative to Vo (set at 1). *p<0.05. Alam et al.[1]
Figure 4:
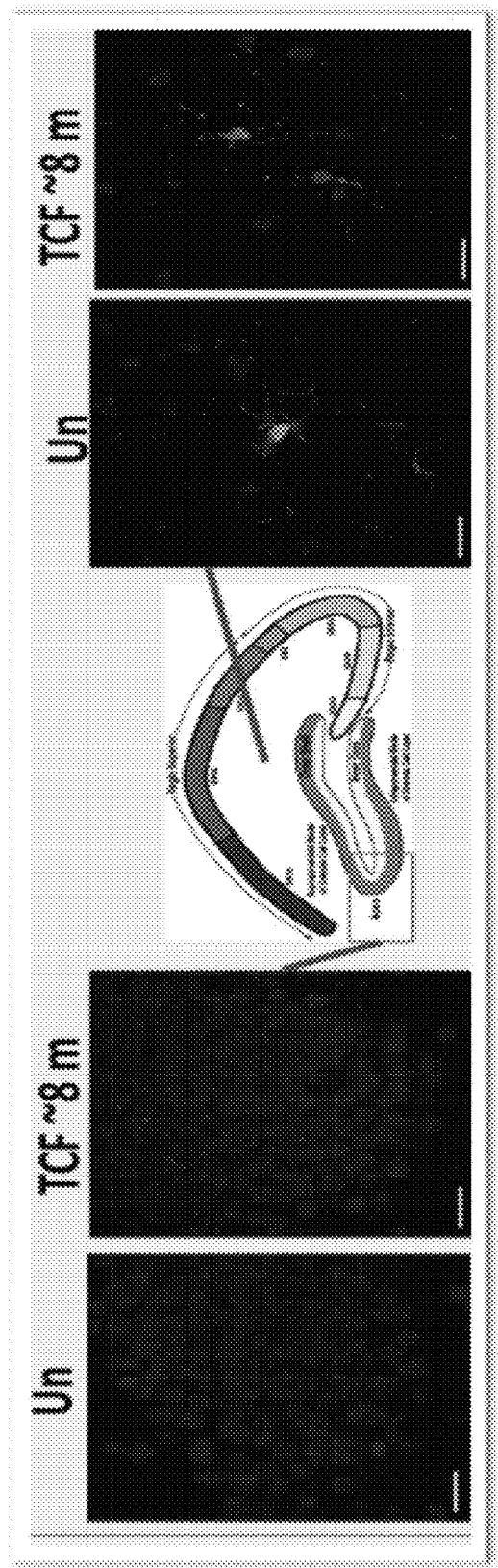
FIG. 4 depicts indirect fluorescence antibody (IFA) detection of microglial cells (green) with anti-Iba1 antibodies in hippocampus of mice untreated (Un) and TCF treated at 8 months. Schematic shows area Blue, DAPI. Scale bar, 40 μm. Per group, n=2 mice. Two sagittal brain sections from each mouse were examined.
Figures 5A, 5B:
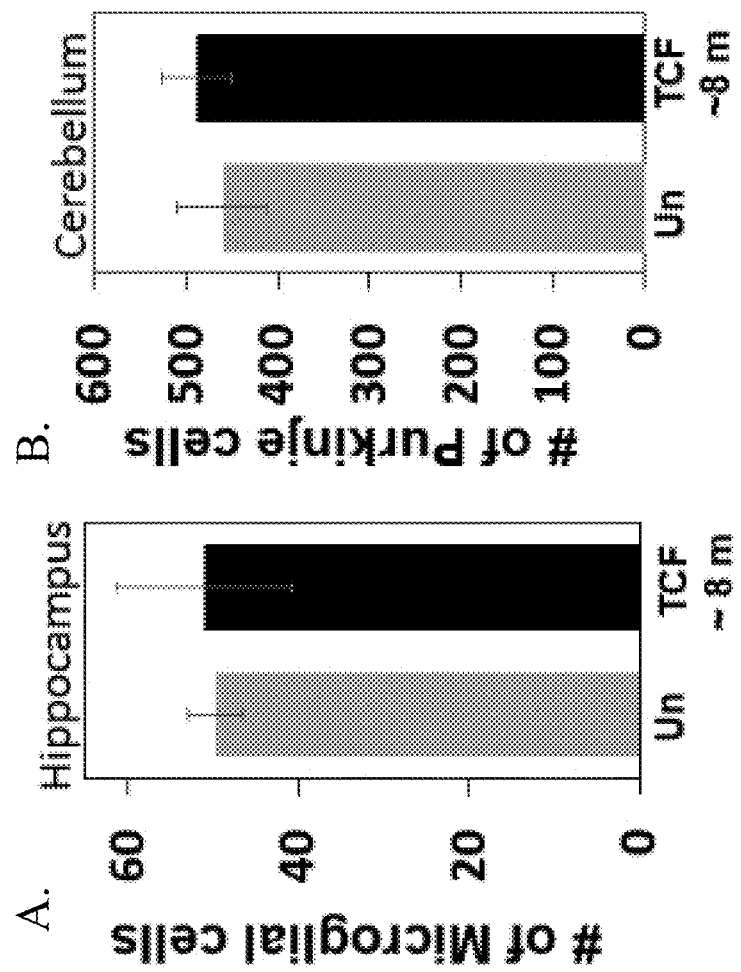
FIGS. 5A-5B depict no loss of Purkinje neurons in the cerebellum or inflammation in the hippocampus for mice treated. A. Quantitative analysis of Iba1 positive microglial cells in the hippocampus, shown in FIG. 4. B. Purkinje cell counts from representative images of IX lobule of the cerebellum from untreated (Un) and TCF treated Balb/c mice at 8 months. For quantitative analyses of TCF treatment, 4 mice were utilized to yield 16 sections (4 per mouse). In untreated animals, 2 mice were utilized to yield 8 sections (4 per mouse).

The theoretical design and proposed action of the TCF is shown in FIG. 1. In mice, TCF boosted Vo levels in plasma and in brain by 2-3 fold (FIGS. 2A-2B). The final maximal levels of Vo in whole brain remained low (~1 ng/mg), but these levels were sufficient to stimulate histone acetylation (FIGS. 3A-3B) and increase Npc1 transcript and protein levels in the brain as well as Npc1$^{nmf164}$ mouse survival (see FIGS. 6B and 6C and FIGS. 2C-E in Alam et al.[1]). Vo in PEG provided no benefit. 2×HPBCD provided no additional benefit compared to 1×HPBCD alone, revealing that Vo in TCF directly impacted survival. Notably, even after 8-12 months of once-weekly ip administration in normal mice the TCF has shown no toxicity in liver or kidney function, does not induce weight loss or long-term behavioral dysfunction. In brains of these animals, there is no loss of Purkinje neurons in the cerebellum or inflammation in hippocampus (FIGS. 4 and 5A-5B).

To test for TCF efficacy in chronic pain we used the spared nerve injury (SNI) model[49] in Sprague-Dawley adult/aging male rats. SNI rats show pain-like behavior, tactile allodynia and cold hyperalgesia, for the rest of life post-SNI. The model has been used extensively, and we and others show mechanistic equivalences for brain adaptations between humans with chronic pain and SNI rats or mice[3,10,17,19,20,50-53].

Figures 6A, 6B, 6C, 6D:
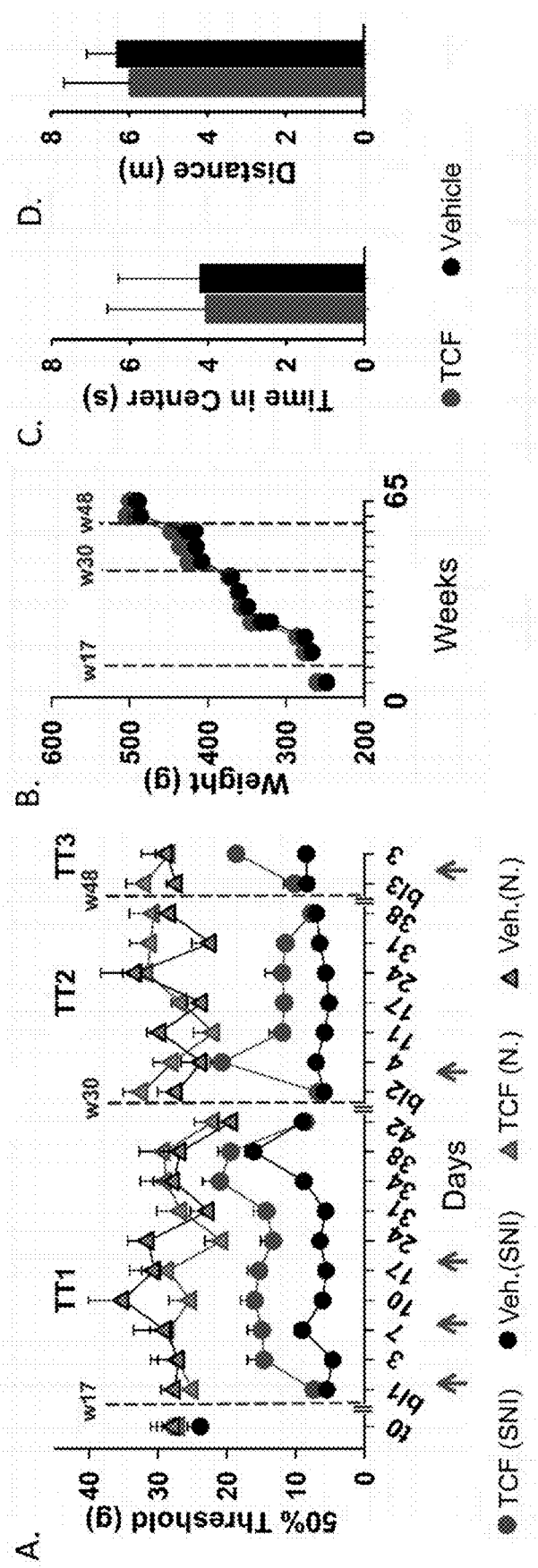
FIGS. 6A-6D depict analgesia, body weight, and mobility of spared nerve injury (SNI) rats treated with TCF or vehicle, monitored over 1 year. A. Tactile sensitivity (50% threshold) monitored for SNI-injured paw, labeled as (SNI), and contralateral uninjured paw, labeled as (N.), before peripheral injury (t0), 17 weeks (w17) after SNI injury (n=17 rats), prior to treatment (Bl1), SNI-paw shows increased sensitivity to touch (allodynia, decreased threshold, reflecting pain), followed by 3 weekly treatments with either TCF (n=9) or Vehicle (Veh., n=8), and monitoring touch sensitivity for 38 days, usually twice/week (3-way, repeated-measures ANOVA 3-RM-ANOVA $F_{8,240}=2.33$ p=0.019 for paw*treatment*time). At week 30 (w30) a new baseline is determined and a single treatment administered in the same groups, and behavior followed for 38 days (3-RM-ANOVA $F_{5,150}=2.22$ p=0.055 for paw*treatment*time). At week 48 (w48) a third treatment trials is initiated (bl3) and tested 3 days later (2-way-ANOVA for paw*treatment $F_{1,28}=5.67$ p=0.024), after which animals were sacrificed and brain tissue and organs collected. B. Body weight over 65 weeks, in TCF and Vehicle treated rats (no group difference). C. Open field, time in center (anxiety assessing measure) (no group difference). D. Open field distance traveled (mobility assessing measure) (no group difference). Red arrows=treatment administration. Error bars are S.E.M.s.

Unilaterally SNI-injured rats when treated with TCF, TCF(SNI) vs. Veh.(SNI) (once/week, 3 treatments), showed robust and sustained analgesia (about 50%) that outlasted the treatment by >20 days. The treatment effect is specific as the uninjured paw sensitivity was not affected, TCF(N.) vs. Veh.(N.). When the procedure was repeated with a single treatment, specific analgesia was sustained for >30 days. A third treatment session (monitoring behavior for 3 days) replicated the specific analgesia observed (FIG. 6A). Body weight did not differ between TCF (n=9) or Vehicle (n=8) treated SNI animals over the 50 weeks (FIG. 6B). Also, anxiety and mobility were not different between the two groups (FIGS. 6C and 6D). TCF treated SNI rats groomed normally and had healthy appearing fur. The long-lasting, relatively large analgesia, with no obvious signs of non-specific effects or off-target toxicity, makes this formulation an exciting candidate to explore for epigenetic control of chronic pain.

REFERENCE LIST

1 Alam, M. S., Getz, M. & Haldar, K. Chronic administration of an HDAC inhibitor treats both neurological and systemic Niemann-Pick type C disease in a mouse model. *Science translational medicine* 8, 326ra323, doi:10.1126/scitranslmed.aad9407 (2016).

2 Committee on Advancing Pain Research, C., and Education. http://www.iom.edu/relievingpain. (2011).

3 Mansour, A. et al. Global disruption of degree rank order: a hallmark of chronic pain. *Scientific reports* 6, 34853, doi:10.1038/srep34853 (2016).

4 Murray, C. J. & Lopez, A. D. Measuring the global burden of disease. *The New England journal of medicine* 369, 448-457, doi:10.1056/NEJMra1201534 (2013).

5 Nascimento, O. J. et al. Neuropathic Pain Treatment: Still a Challenge. *Neurol Int* 8, 6322, doi:10.4081/ni.2016.6322 (2016).

6 CDC. http://www.cdc.gov/drugoverdose/data/overdose.html, 2016).

7 Khangura, R. K., Bali, A., Jaggi, A. S. & Singh, N. Histone acetylation and histone deacetylation in neuropathic pain: An unresolved puzzle? *European journal of pharmacology* 795, 36-42, doi:10.1016/j.ejphar.2016.12.001 (2017).

8 Wang, W., Cui, S. S., Lu, R. & Zhang, H. Is there any therapeutic value for the use of histone deacetylase inhibitors for chronic pain? *Brain research bulletin* 125, 44-52, doi:10.1016/j.brainresbull.2016.04.010 (2016).

9 Massart, R. et al. Overlapping signatures of chronic pain in the DNA methylation landscape of prefrontal cortex and peripheral T cells. *Scientific reports* 6, 19615, doi: 10.1038/srep19615 (2016).

10 Baliki, M. N., Chang, P. C., Baria, A. T., Centeno, M. V. & Apkarian, A. V. Resting-state functional reorganization of the rat limbic system following neuropathic injury. *Scientific reports* 4, 6186, doi:10.1038/srep06186 (2014).

11 Baliki, M. N. & Apkarian, A. V. Nociception, Pain, Negative Moods, and Behavior Selection. *Neuron* 87, 474-491, doi:10.1016/j.neuron.2015.06.005 (2015).

12 Baliki, M. N. et al. Corticostriatal functional connectivity predicts transition to chronic back pain. *Nature neuroscience* 15, 1117-1119, doi:10.1038/nn.3153 (2012).

13 Hashmi, J. A. et al. Shape shifting pain: chronification of back pain shifts brain representation from nociceptive to emotional circuits. *Brain: a journal of neurology* 136, 2751-2768, doi:10.1093/brain/awt211 (2013).

14 Baliki, M. N., Geha, P. Y., Fields, H. L. & Apkarian, A. V. Predicting value of pain and analgesia: nucleus accumbens response to noxious stimuli changes in the presence of chronic pain. *Neuron* 66, 149-160, doi:50896-6273(10)00171-6 [pii]10.1016/j.neuron.2010.03.002 (2010).

15 Mansour, A. R. et al. Brain white matter structural properties predict transition to chronic pain. *Pain* 154, 2160-2168, doi:10.1016/j.pain.2013.06.044 (2013).

16 Mutso, A. A. et al. Reorganization of Hippocampal Functional Connectivity with Transition to Chronic Back Pain. *Journal of neurophysiology*, doi:10.1152/jn.00611.2013 (2013).

17 Mutso, A. A. et al. Abnormalities in hippocampal functioning with persistent pain. *The Journal of neuroscience: the official journal of the Society for Neuroscience* 32, 5747-5756, doi:10.1523/JNEUROSCI.0587-12.2012 (2012).

18 Vachon-Presseau, E. et al. Corticolimbic anatomical characteristics predetermine risk for chronic pain. *Brain: a journal of neurology* In Press, doi:10.1093/brain/aww100 (2016).

19 Ren, W. et al. The indirect pathway of the nucleus accumbens shell amplifies neuropathic pain. *Nature neuroscience* 19, 220-222, doi:10.1038/nn.4199 (2016)

20 Chang, P. C. et al. Role of nucleus accumbens in neuropathic pain: linked multi-scale evidence in the rat transitioning to neuropathic pain. *Pain* 155, 1128-1139, doi:10.1016/j.pain.2014.02.019 (2014).

21 Chang, P. C. et al. Novel method for functional brain imaging in awake minimally restrained rats. *Journal of neurophysiology* 116, 61-80, doi:10.1152/jn.01078.2015 (2016).

22 Breivik, H., Collett, B., Ventafridda, V., Cohen, R. & Gallacher, D. Survey of chronic pain in Europe: prevalence, impact on daily life, and treatment. *Eur J Pain* 10, 287-333, doi:10.1016/j.ejpain.2005.06.009 (2006).

23 Harstall, C. & Ospina, M. How prevalent is chronic pain? *Pain Clinical Updates* 11 (2003).

24 Janssen, A. P. S. a. & Pharmaceutica. Chronic Pain in America: Roadblocks to Relief, a study conducted by Roper StarchWorldwide for American Academy of Pain Medicine, American Pain Society and Janssen Pharmaceutica, <http://www.ampainsoc.org/links/roadblocks/> (2010).

25 Torres-Perez, J. V. et al. Phosphorylated Histone 3 at Serine 10 Identifies Activated Spinal Neurons and Contributes to the Development of Tissue Injury-Associated Pain. *Scientific reports* 7, 41221, doi:10.1038/srep41221 (2017).

26 Machelska, H. & Celik, M. O. Recent advances in understanding neuropathic pain: glia, sex differences, and epigenetics. *F1000Research* 5, 2743, doi:10.12688/f1000research.9621.1 (2016).

27 Descalzi, G. et al. Epigenetic mechanisms of chronic pain. *Trends in neurosciences* 38, 237-246, doi:10.1016/j.tins.2015.02.001 (2015).

28 Alvarado, S. et al. An epigenetic hypothesis for the genomic memory of pain. *Front Cell Neurosci* 9, 88, doi:10.3389/fncel.2015.00088 (2015).

29 Giannini, G., Cabri, W., Fattorusso, C. & Rodriquez, M. Histone deacetylase inhibitors in the treatment of cancer: overview and perspectives. *Future Med Chem* 4, 1439-1460, doi:10.4155/Fmc.12.80 (2012).

30 Chessum, N., Jones, K., Pasqua, E. & Tucker, M. Recent advances in cancer therapeutics. *Prog Med Chem* 54, 1-63, doi:10.1016/bs.pmch.2014.11.002 (2015).

31 Falkenberg, K. J. & Johnstone, R. W. Histone deacetylases and their inhibitors in cancer, neurological diseases and immune disorders (vol 13, pg 673, 2014). *Nature Reviews Drug Discovery* 14, 219-219, doi:10.1038/nrd4579 (2015).

32 Xu, W. S., Parmigiani, R. B. & Marks, P. A. Histone deacetylase inhibitors: molecular mechanisms of action. *Oncogene* 26, 5541-5552, doi:10.1038/sj.onc.1210620 (2007).

33 Dokmanovic, M., Clarke, C. & Marks, P. A. Histone deacetylase inhibitors: Overview and perspectives. *Mol Cancer Res* 5, 981-989, doi:10.1158/1541-7786.Mcr-07-0324 (2007).

34 Di, X. J., Han, D. Y., Wang, Y. J., Chance, M. R. & Mu, T. W. SAHA Enhances Proteostasis of Epilepsy-Associated alpha 1(A322D)beta 2 gamma 2 GABA(A) Receptors. *Chem Biol* 20, 1456-1468, doi:10.1016/j.chembiol.2013.09.020 (2013).

35 Yang, C. Z. et al. Histone deacetylase inhibitors increase glucocerebrosidase activity in Gaucher disease by modulation of molecular chaperones. *P Natl Acad Sci USA* 110, 966-971, doi:10.1073/pnas.1221046110 (2013).

36 Calamini, B. & Morimoto, R. I. Protein Homeostasis as a Therapeutic Target for Diseases of Protein Conformation. *Curr Top Med Chem* 12, 2623-2640 (2012).

37 Venkatraman, A. et al. The histone deacetylase HDAC3 is essential for Purkinje cell function, potentially complicating the use of HDAC inhibitors in SCA1. *Hum Mol Genet* 23, 3733-3745, doi:10.1093/hmg/ddu081 (2014).

38 Cherng, C. H. et al. Baicalin ameliorates neuropathic pain by suppressing HDAC1 expression in the spinal cord of spinal nerve ligation rats. *J Formos Med Assoc* 113, 513-520, doi:10.1016/j.jfma.2013.04.007 (2014).

39 Chiechio, S. et al. Epigenetic modulation of mGlu2 receptors by histone deacetylase inhibitors in the treatment of inflammatory pain. *Mol Pharmacol* 75, 1014-1020, doi:10.1124/mol.108.054346 (2009).

40 Zammataro, M., Sortino, M. A., Parenti, C., Gereau, R. W. t. & Chiechio, S. HDAC and HAT inhibitors differently affect analgesia mediated by group II metabotropic glutamate receptors. *Molecular pain* 10, 68, doi:10.1186/1744-8069-10-68 (2014).

41 Bai, G., Wei, D., Zou, S., Ren, K. & Dubner, R. Inhibition of class II histone deacetylases in the spinal cord attenuates inflammatory hyperalgesia. *Molecular pain* 6, 51, doi:10.1186/1744-8069-6-51 (2010).

42 Zhang, Z., Cai, Y. Q., Zou, F., Bie, B. & Pan, Z. Z. Epigenetic suppression of GAD65 expression mediates persistent pain. *Nat Med* 17, 1448-1455, doi:10.1038/nm.2442 (2011).

43 Tajerian, M. et al. Peripheral nerve injury is associated with chronic, reversible changes in global DNA methylation in the mouse prefrontal cortex. *PloS one* 8, e55259, doi:10.1371/journal.pone.0055259 (2013).

44 Imai, S. et al. Change in microRNAs associated with neuronal adaptive responses in the nucleus accumbens under neuropathic pain. *The Journal of neuroscience: the official journal of the Society for Neuroscience* 31, 15294-15299, doi:10.1523/JNEUROSCI.0921-11.2011 (2011).

45 Tran, L., Schulkin, J., Ligon, C. O. & Greenwood-Van Meerveld, B. Epigenetic modulation of chronic anxiety and pain by histone deacetylation. *Molecular psychiatry* 20, 1219-1231, doi:10.1038/mp.2014.122 (2015).

46 Simon, R. P., Robaa, D., Alhalabi, Z., Sippl, W. & Jung, M. KATching-Up on Small Molecule Modulators of Lysine Acetyltransferases. *J Med Chem* 59, 1249-1270, doi:10.1021/acs.jmedchem.5b01502 (2016).

47 Roche, J. & Bertrand, P. Inside HDACs with more selective HDAC inhibitors. *Eur J Med Chem* 121, 451-483, doi:10.1016/j.ejmech.2016.05.047 (2016).
48 Vachon-Presseau, E. et al. The Emotional Brain as a Predictor and Amplifier of Chronic Pain. *J Dent Res* 95, 605-612, doi:10.1177/0022034516638027 (2016).
49 Decosterd, I. & Woolf, C. J. Spared nerve injury: an animal model of persistent peripheral neuropathic pain. *Pain* 87, 149-158 (2000).
50 Moore, K. A. et al. Partial peripheral nerve injury promotes a selective loss of GABAergic inhibition in the superficial dorsal horn of the spinal cord. J Neurosci. 22, 6724-6731 (2002).
51 Scholz, J. et al. Blocking caspase activity prevents transsynaptic neuronal apoptosis and the loss of inhibition in lamina II of the dorsal horn after peripheral nerve injury. *J Neurosci.* 25, 7317-7323 (2005).
52 Apkarian, A. V. et al. Role of adult hippocampal neurogenesis in persistent pain. *Pain* 157, 418-428, doi: 10.1097/j.pain.0000000000000332 (2016).
53 Lee, M. et al. Activation of corticostriatal circuitry relieves chronic neuropathic pain. *The Journal of neuroscience: the official journal of the Society for Neuroscience* 35, 5247-5259, doi:10.1523/JNEUROSCI.3494-14.2015 (2015).
54 Kelly, W. K. et al. Phase I clinical trial of histone deacetylase inhibitor: suberoylanilide hydroxamic acid administered intravenously. *Clin Cancer Res* 9, 3578-3588 (2003).
55 MacCoun, R. P., S. Blind analysis: Hide results to seek the truth. *Nature* 526, 187-189 (2015).
56 Winston, J. H., Li, Q. & Sarna, S. K. Chronic prenatal stress epigenetically modifies spinal cord BDNF expression to induce sex-specific visceral hypersensitivity in offspring. *Neurogastroenterol Motil* 26, 715-730, doi: 10.1111/nmo.12326 (2014).
57 Rossi, F., Perale, G., Papa, S., Forloni, G. & Veglianese, P. Current options for drug delivery to the spinal cord. *Expert Opin Drug Deliv* 10, 385-396, doi:10.1517/17425247.2013.751372 (2013).
58 Slotkin, J. R. et al. Sustained Local Release of Methylprednisolone From a Thiol-Acrylate Poly(Ethylene Glycol) Hydrogel for Treating Chronic Compressive Radicular Pain. *Spine* 41, E441-448, doi:10.1097/BRS.0000000000001309 (2016).
59 Monteiro Nascimento, M. H. et al. Cyclodextrin-Based Delivery Systems for Arthritic Diseases: From Development to Experimental Therapeutics. *Curr Pharm Des* 21, 4907-4916 (2015).
60 Anders, S. & Huber, W. Differential expression analysis for sequence count data. *Genome Biol* 11, doi:ARTN R10610.1186/gb-2010-11-10-r106 (2010).
61 Dillies, M. A. et al. A comprehensive evaluation of normalization methods for Illumina high-throughput RNA sequencing data analysis. *Brief Bioinform* 14, 671-683, doi:10.1093/bib/bbs046 (2013).
62 Davis, D. A. G., M. E.; Farmer, M. A.; Baria, A. T.; Apkarian, A. V. Identifying brain nociceptive information transmission in patients with chronic somatic pain. *Pain reports* 1, e575-e577 (2016).
63 Apkarian, A. V. et al. Chronic pain patients are impaired on an emotional decision-making task *Pain* 108, 129-136 (2004).
64 Small, D. M. & Apkarian, A. V. Increased taste intensity perception exhibited by patients with chronic back pain. *Pain* 120, 124-130 (2006).
65 Millecamps, M. et al. D-cycloserine reduces neuropathic pain behavior through limbic NMDA-mediated circuitry. *Pain* (2006).
66. PCT Application No. PCT/US2015/035438 entitled "Composition and Method for the Treatment of Neurological Diseases and Cerebral Injury."

Example 2

Histone deacetylase inhibitors (HDACi) are emerging therapeutics for a broad range of diseases including cancer and neurodegeneration[1-4]. They block HDAC enzymes, to promote acetylation of both histones and non-histone proteins to elicit complex cellular changes[5,6]. HDACi-induced histone modifications have been shown to increase or decrease transcriptional expression of mutated target gene(s) in many genetic diseases as well as indirect benefit through modulation of chaperone and proteostatic networks[7-9]. Due to their broad effects on transcription, it is particularly important to maximize HDACi efficacy while limiting dose. We previously reported on development and validation of a therapeutic strategy of a triple combination formulation (TCF) of the HDACi vorinostat (Vo) that enabled lowering concentrations of Vo to treat cerebral disease as well as inflammation in liver and spleen, in a mouse model of a fatal cerebellar disorder Niemann-Pick Type C (NPC) disease[10].

NPC is caused by defect in either Npc1 or Npc2 genes[11]. It is a rare autosomal recessive neurodegenerative disease. 95% of cases are due to defect in Npc1. Cells with defects in either Npc genes accumulate cholesterol late endosomes/lysosomes[12,13]. A point mutation in Npc1 gene that blocks cholesterol transport in cells is causative for neurodegeneration in a mouse model[14]. At the organismal level, in the central nervous system (CNS), Npc1 is essential for myelination[15] and likely additional functions[16]. Neurodegeneration is a hallmark of clinical NPC disease. Disease progression can be heterogeneous and slow but once initiated, is invariably fatal[11]. Splenomegaly and hepatomegaly are common presenting symptoms in pediatric cases followed by neurocognitive and neuromuscular degeneration[17]. Lung disease is prominent and can even be cause of death[18,19].

Presently the only available treatment for NPC is miglustat (Zavesca™), an iminosugar that decreases glycosphingolipid accumulation in type1 Gaucher's disease[20,21], was approved for NPC treatment in Europe, Canada and Japan but denied FDA approval (although it is prescribed off label in the US). Miglustat may confer mild improvement in specific clinical symptoms but fails to prevent disease progression[22,23]. 2-Hydroxy propyl beta cyclodextrin (HPBCD) is being investigated as an emerging therapy[24,25]. It chelates cholesterol but does not cross the blood brain barrier[26]. Therefore, to treat neurological disease HPBCD must be directly delivered to the central nervous system (CNS;[27,28]) which carries procedural risk of life-long therapy. Systemic delivery is needed to improve liver and other visceral organs but inexplicably, HPBCD is excluded from lung[29,30] and therefore of little benefit to end-stage advanced and frequently fatal bronchial disease. Arimoclomol is another emergent therapy for NPC[31], but its benefit for systemic disease especially in treatment of lung inflammatory disease remains unknown.

The TCF combines HPBCD, PEG, and Vo in a defined formulation N. Upon systemic injection, it increases the plasma exposure of Vo and boosts its delivery across the BBB to stimulate histone acetylation there. Although mice chronically treated for close to a year showed no metabolic toxicity[10], the effect of long term TCF exposure on key neurons, brain areas and overall progression of symptoms of neurodegeneration that mimic human disease, have not been assessed. Further, while HPBCD reduces systemic inflammation[10,24,29] it is excluded from lungs[29,30] and therefore whether the TCF promotes Vo delivery and therapeutic action in lungs remains unknown. Our findings on these points advance development of a new HDACi therapeutic strategy to treat NPC and other difficult-to-treat disorders that may benefit from epigenetic therapy.

Methods

Materials—All fine chemicals including 2-hydroxypropyl-β-cyclodextrin (HPBCD) and polyethylene glycol 400 (PEG) were procured from Sigma (St Louis, Mo., USA) unless otherwise indicated. Vorinostat was from Selleck Chemicals (Houston, Tex., USA).

Animals—Npc1$^{nmf164}$ is a BALB/c strain carry a D1005G (A to G at cDNA bp 3163) mutation in the Npc1 gene 32. A breeding pair of mutant mice were obtained from Robert P. Erickson, University of Arizona Health Sciences Center, Tucson, Ariz., USA and is available at The Jackson Laboratories. Homozygous mutants (Npc1$^{nmf164}$) along with wild-type littermates (Npc1$^{+/+}$), were generated in house by crossing heterozygous mutant (Npc1$^{+/nmf164}$) males and females and genotyped as previously described[10]. Wild type Balb/c mice were procured from Envigo (Indianapolis, Ind., USA).

Drug injection and organ harvest—The Triple combination formulation (TCF) is a mixture of vorinostat (50 mg/kg), HPBCD (2000 mg/Kg)), PEG 400 (45%) and DMSO (5%). Vorinostat (50 mg/Kg) was made in 5% DMSO and 45% PEG. HPBCD was a 20% (w/v) solution and given dose of 2000 mg/Kg. Detailed methodology on preparing drug solutions have been descried earlier[10]. To enable comparative studies with prior regiments, all mice were given two doses of HPBCD at P7 and P15. From P21 onwards, mice received either HPBCD alone or TCF, as indicated. Vo was also initiated at P21. Injections were administered weekly through the intraperitoneal (i.p) route (and the injection volume used was 10 ml/Kg body weight across all treatment groups). For lung histopathology, Npc1$^{nmf164}$ mice were analyzed at 100-109 days of age. Long-term safety was assessed for 8-10 months either in Npc1$^{+/nmf164}$ or commercially purchased wild type Balb/c mice. The animals were sacrificed by asphyxiation using CO2 and harvested organs were immersed fixed in 10% neutral buffered formalin (~4% formaldehyde) for 24 hours at RT and subsequently stored in 70% alcohol until transfer to paraffin.

Nissl and H&E staining—Paraffin-embedded sections (4-5 μm) were dewaxed in xylene and alcohol. For Nissl, brain sections were stained with acidified 0.1% cresyl violet for 7 min followed by two incubations in 95% ethanol of 5 min each. The sections were cleared in xylene and mounted in cytoseal XYL (Thermo Scientific, Kalamazoo, USA). H&E staining of brain and lung tissues was carried out by AML laboratories according to standard methods[33]. Images were visualized with DPlan Apo 40×/1.00 oil immersion objective lens (Nikon) and captured on a Nikon Olympus microscope, using a Nikon digital DS-Fi1-U2 camera controlled by NIS-Elements F3.0 Nikon software (all from Nikon Instruments INC, Tokyo, Japan).

Iba1 immunostaining of brain sections—Paraffin-embedded brain sections (4-5 μm) were dewaxed in xylene and alcohol. Iba1 antigen was retrieved by boiling the sections in acidic condition for 30 min. Blocking was done with 2% goat serum for 30 min at RT. Sections were incubated with anti-Iba1 (1:500, 019-19741, Wako Chemicals) overnight at 4° C. FITC-conjugated secondary IgG antibodies (MP Biomedicals, Solon, Ohio, USA) were used at a dilution of 1:200. Nuclei were stained with DAPI (0.5 μg/ml) and mounting was done using Vectashield (Vector laboratories). Sections were visualized with 40× oil-immersion objective lens (NA 1.35) and image collection was performed using an Olympus IX inverted fluorescence microscope and a Photometrix cooled CCD camera (CH350/LCCD) driven by DeltaVision software from Applied Precision (Seattle, Wash., USA). DeltaVision software (softWoRx) was used to deconvolve these images. Images are single optical sections. Images were analyzed using 'softWoRx' or 'ImageJ' software (NIH, MD, USA).

Quantification of Vo in lungs—Npc1$^{+/nmf164}$ mice (age 6-7 weeks) were given intraperitoneal injections of either Vo (50 mg/Kg in 45% PEG and 5% DMSO) or TCF (Vo 50 mg/Kg+HPBCD, 2000 mg/Kg+PEG, 45%+DMSO, 5%). At 30 min and 1 h post injection, mice were asphyxiated with CO2, blood was drawn by cardiac puncture and organs were perfused with 20 ml ice-cold PBS through the ventricle. Harvested lungs were cut into small pieces (4-6 mm2) and flash frozen in liquid nitrogen. The quantification of vorinostat was done by Metabolite Profiling Facility, Bindley Bioscience Center, Purdue University, Ind., USA. The detailed methods are as described earlier[10]. Briefly, the tissue was homogenized using a Precelly bead homogenizer system utilizing ceramic CK 14 beads. 2 ng of deuterated internal standard (d5-Vorinostat, Toronto Research Chemicals, Ontario, Canada) was added to lung homogenate prior to liquid extraction with acetonitrile. Prior to analysis, samples were reconstituted in 100 μL of 50% water/50% acetonitrile. An Agilent 1200 Rapid Resolution liquid chromatography (HPLC) system coupled to an Agilent 6460 series triple quadrupole mass spectrometer (MS/MS) was used to analyze vorinostat. The data were obtained in positive electrospray ionization (ESI) mode and quantitated by monitoring the following transitions: for Vorinostat, 265→232 with a collision energy of 5 V and for d5-Vorinostat, 270→237 with collision energy of 5 V.

Results

Assessment of chronic TCF-treatment in cerebellar and hippocampal regions as well as a neurobehavioral/cognitive disease score in mice. HDACs are important enzymes and their functions are required in brain development[34-36], in particular, HDAC3 knockdown blocked development of Purkinje neurons[37]. It has therefore been hypothesized that long-term HDACi treatment may adversely affect the brain. However, we have reported that weekly administration of the TCF in Npc1$^{nmf164}$ mice prevented loss of Purkinje cell neurons[10]. Since Vorinostat from the TCF peaks at 30 minutes and is rapidly cleared from the brain and plasma[10], our findings suggested that epigenetic modulation associated with transient block of HDAC3 (as well as other HDACs) may be tolerated and benefit NPC-diseased animals.

Figures 7A, 7B, 7C:
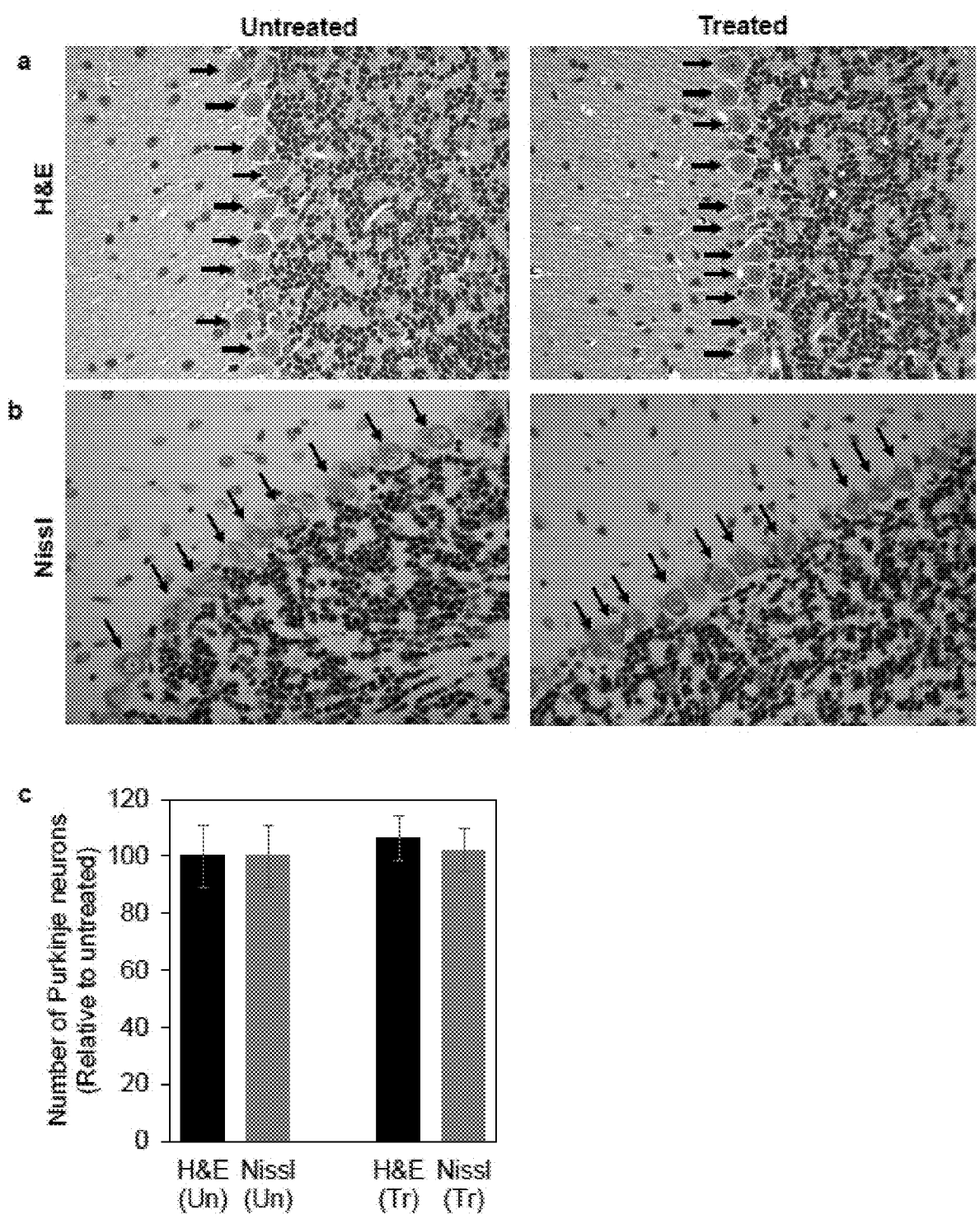
FIGS. 7A-7C show analysis of Purkinje neurons in long-term TCF-treated mice by (FIG. 7A) H&E and (FIG. 7B) Nissl staining. Representative micrographs of cerebellum from untreated (108 days) and TCF-treated healthy (Npc1$^{+/nmf164}$, 225-265 days) mouse are shown. Purkinje neurons are shown by black arrows. The images shown are representative from four mice in each group.

But the effects of TCF on neurons in normal animal brain remain unaddressed. Since Purkinje are major neurons requiring HDAC function, we used them as a sentinel neuron for effects of extended TCF-treatment in healthy animals. We administered weekly TCF to heterozygous, healthy 'control' animals for 2-3 fold longer (240-300 days) than the 100 day-efficacy period in Npc1$^{nmf164}$ mice. As shown in FIG. 7A, H&E staining failed to show any change in histological features of Purkinje cells in the cerebellum. Nissl staining suggested they were intact neurons (FIG. 7B). Quantitative analyses of both H&E- and Nissl-staining confirmed that the TCF even on extended treatment did not lead to death and loss of Purkinje cells (FIG. 7C). These data indicate that recurrent, short-lived exposure of low concentrations of vorinostat does not cause neuronal loss, even as it is sufficient to trigger sustained epigenetic effects.

Figures 8A, 8B, 8C:
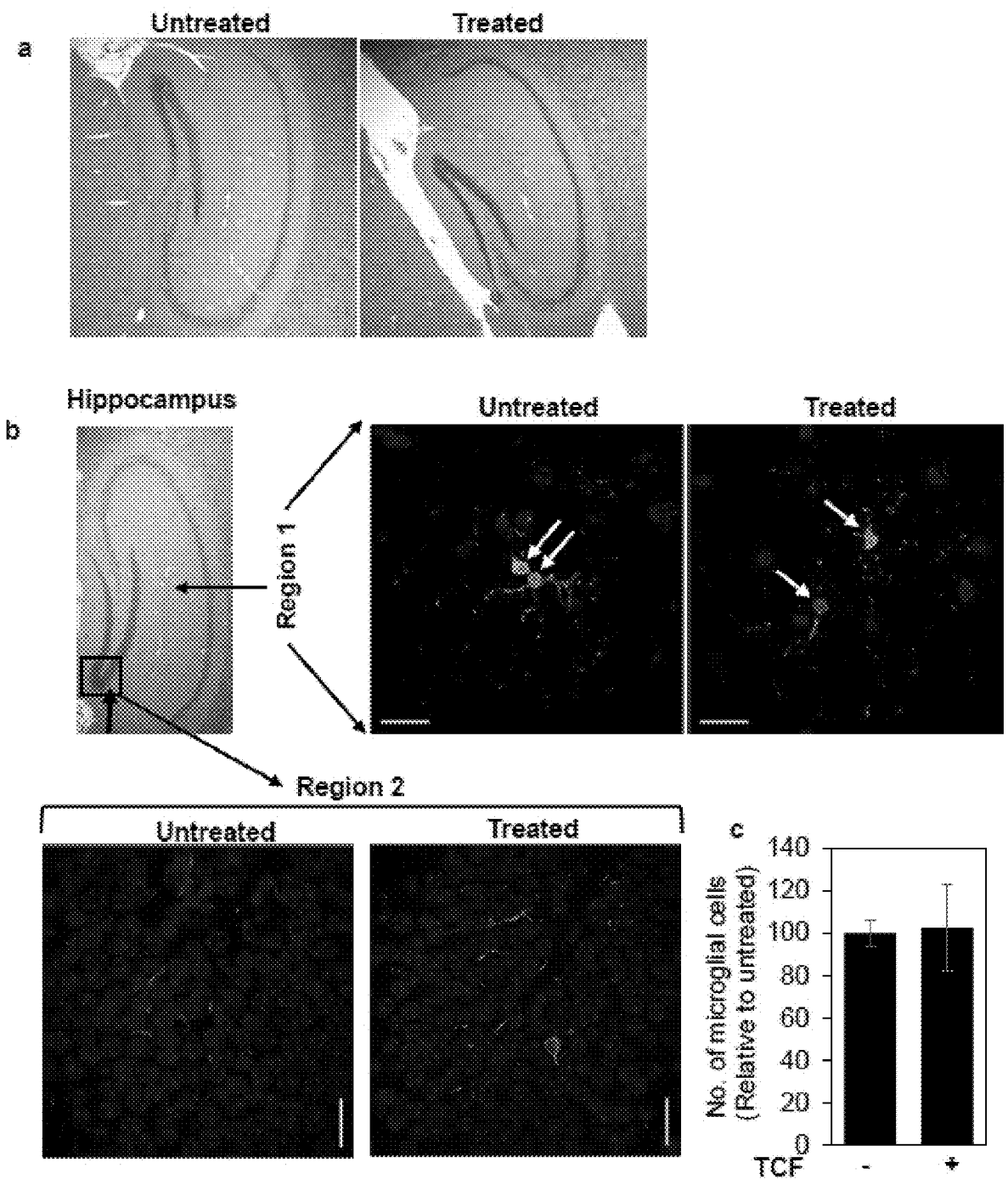
FIGS. 8A-8C show safety assessment in the hippocampus of mice after chronic treatment with TCF for long-term.

Activation of microglial cells marks neuroinflammation, an early sign of neuronal dysfunction[38,39]. We have previously shown that microglia stained with antibodies to the Iba inflammatory marker accumulate in the hippocampus of Npc1$^{nmf164}$ mice[10]. Further at ~100 days after weekly TCF treatment, Iba staining is reduced suggesting that TCF can target inflammatory dysfunction in the hippocampus. Comparable H&E staining is seen in representative hippocampal regions from mice exposed to weekly TCF treatment for 225-265 days compared to untreated animals at 100-110 days (FIG. 8A) with each showing only a few resident microglial cells (FIG. 8B). Quantitative analysis showed no significant difference in the number of microglial cells untreated and chronically TCF-treated mice (FIG. 8C), suggesting that despite the fact that Vo is predicted to transcriptionally activate numerous target genes, the TCF does not induce an inflammatory response broadly damaging to neurons.

Figures 9A, 9B:
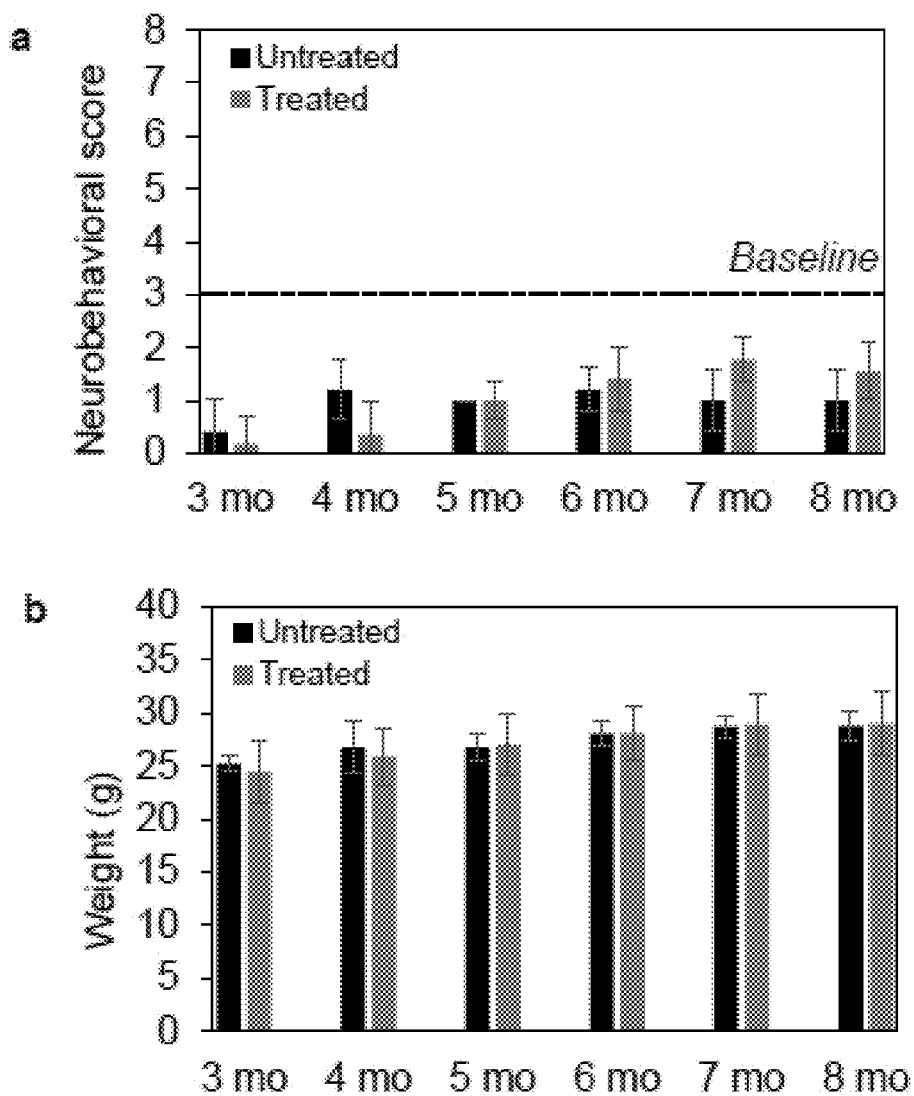
FIGS. 9A-9B show assessment of chronic TCF treatment on neurobehavioral/cognitive disease score and body weight in wild type Balb/c mice.

Clinically NPC disease is defined by major and minor symptomatic domains, whose severity has been quantified to monitor the natural history of the disease[40]. While awaiting plasma biomarkers[41-44] symptom scoring continues as an important index of progressive disease. We previously created a disease severity scale for murine NPC that captures major patient disease domain scored in a defined indicated range and whose sum provides the cumulate disease score, (with a maximal score of 13;[10]). Because older healthy animals, particularly males, often displayed poor grooming and slight impairment in limb tone onwards of 100 days, a cumulative score of 3 or higher reliably flags onset of symptomatic disease. Untreated Npc1$^{nmf164}$ mice progress to a score of 10-13 by 100 days, but TCF affords significant reduction to 4-5 when administered over the same period[10] to render functional benefit to major symptomatic domains of neurological disease that include ambulation, cognition, motor control and dysphagia. In contrast, the cumulative score remained below baseline in healthy wild type mice receiving chronic weekly administration of TCF (FIG. 9A, FIG. 13; with indicated scores of 1-2 that also appear in untreated animals, as expected due to their poor grooming). There was also no change in animal weight (FIG. 9B) showing TCF-treatment did not impair overall nutrient consumption and utilization (which marks mid- and end-stage neurological disease[10]).

TCF increases Vo levels in lung. As previously reported the TCF is a triple combination formulation containing Vo, HPBCD, and PEG[10]. In prior work we found that 1 h after injection of TCF, Vo concentrations in mouse plasma were 3 fold higher compared to the levels observed when Vo was administered in PEG alone[10]. Vo levels in the brain were also significantly boosted in TCF-injected mice[10]. These data suggested that the HPBCD was a major contributor to the pharmacokinetic (PK) effect in plasma and brain. Further examination of brain, liver, and spleen suggested the TCF could treat both neurological as well as systemic NPC disease in mice. However, since HPBCD is known to be excluded from lungs[29,30], it remained unclear whether the TCF increased exposure of Vo and/or benefit lung disease.

Figure 10:
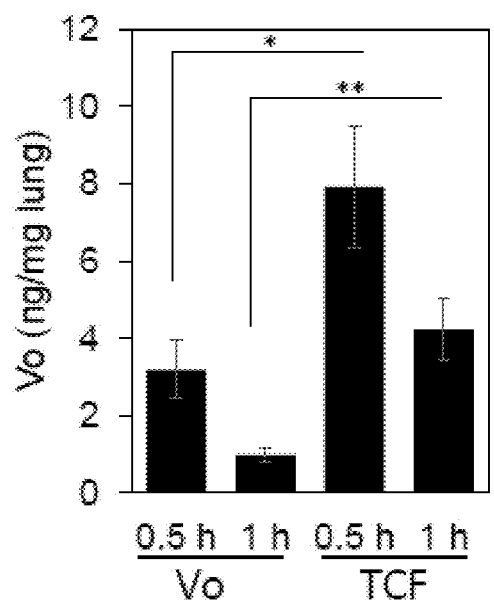
FIG. 10 shows increased lung concentration of Vo in TCF injected mice. Npc1$^{+/nmf164}$ injected i.p. with Vo or TCF. At indicated times, animals sacrificed, perfused with PBS and Vo concentration in lungs were determined by mass spectrometry. n=5. h, hour. *p=0.02, TCF vs Vo 0.5 h, and **p=0.014 TCF vs Vo, 1 h, two tailed Student's t test.

As shown in FIG. 10, animals injected with Vo in PEG alone showed a mean concentration of 3.2 ng/mg Vo in lungs at 30 minutes, which decreased to 1 ng/mg by 60 min. After TCF injection, Vo concentration reached 7.9 ng/mg at 30 min and then declined to 4.2 ng/mg at 60 min. These data suggested that the TCF boosted Vo entry into lungs, likely due to the (2.5-3 fold) plasma pharmacokinetic effect (previously reported in[10]). Vo concentrations (of 4.2 ng/mg) detected at 60 min in TCF-treated animals were reduced by 45-50% reduction from levels seen at 30 min. Animals injected with Vo in PEG showed a 65-70% reduction over the same period, suggesting that in addition to boosting peak concentrations, the TCF may also slow down Vo clearance from lungs and both effects may increase levels and exposure of Vo in lungs.

Figure 11:
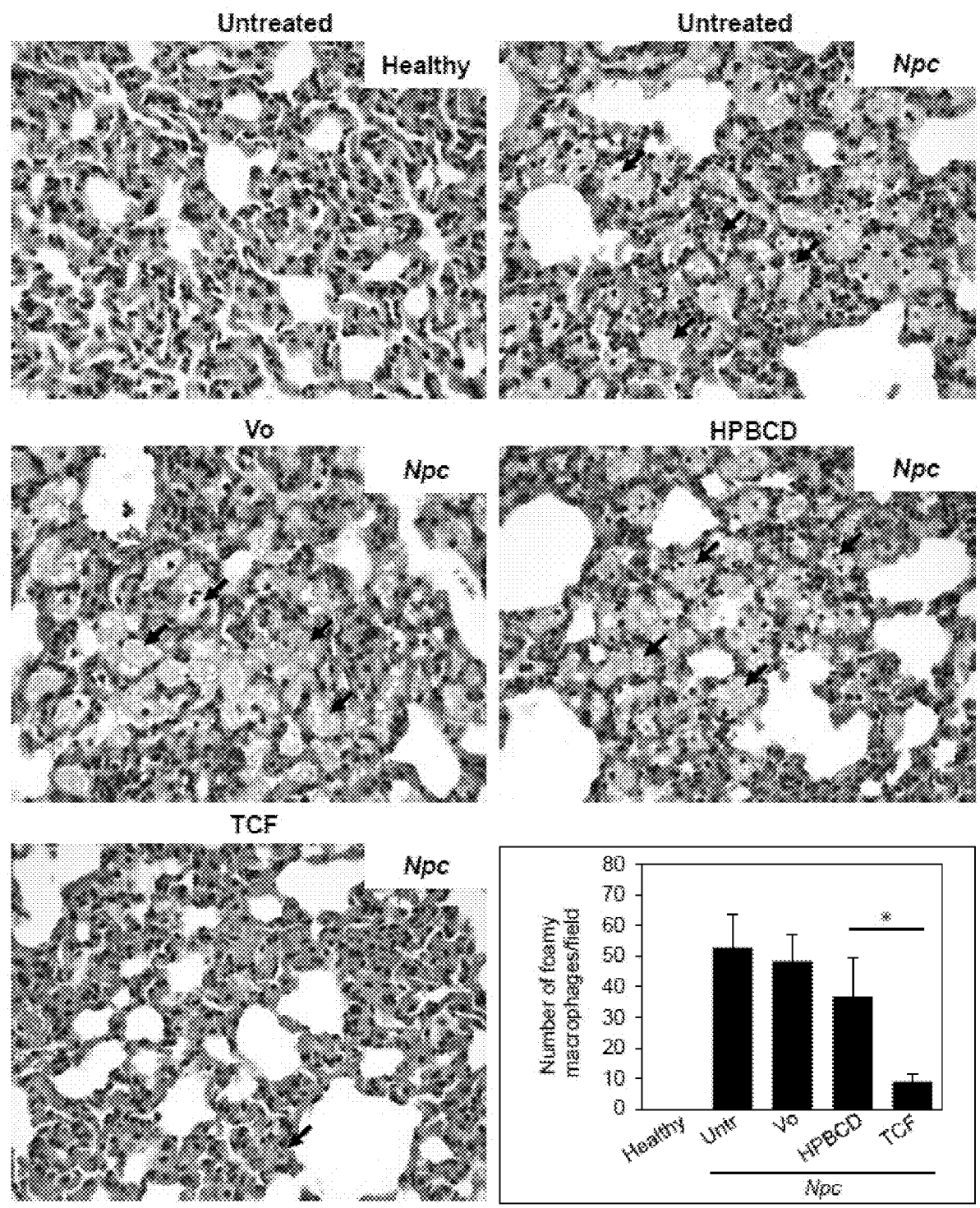
FIG. 11 shows efficacy of TCF in reducing the accumulation of foamy macrophages in the lungs of Npc mice. H&E stained micrographs showing foamy macrophages (indicated by black arrows) at 100 days of age in the lung of Npc1$^{+/nmf164}$ (healthy control) and Npc1$^{nmf164}$ ($^{Npc}$) mutant mice treated as indicated. Foamy macrophages were abundant in untreated Npc mice. Treatment with Vo (vorinostat) or HPBCD had no effect whereas TCF treatment greatly reduced the accumulation of foamy macrophages. Images were taken with 40× objective lens and are representative of 4 mice in each group. Number of mice in each group=4. For quantitation, 10-15 random fields were analyzed per lung section. Untr, Untreated.*p=0.02, TCF vs HPBCD, two-tailed Mann-Whitney test.

TCF reduces the accumulation of foamy macrophages in the lungs of Npc1$^{nmf164}$ mice. Previous studies[24,29,45] have shown that the systemic delivery of HPBCD in NPC mice fails to alleviate lung disease (because HPBCD may not be able to reach the tissue). Since HPBCD is a major component of the TCF, this raised question on whether the formulation could alleviate lung disease even as it boosted Vo delivery to other organs. To test this, we undertook histochemical analysis of lungs from control and treated mice. Animals were examined at 100 days of age, since in prior work with the Npc1$^{nmf164}$ mouse model we have shown that this is a time of significant neurological disease responsive to treatment by TCF. As shown in FIG. 11, H&E stained micrographs revealed accumulation of large number of foamy macrophages in the lungs of untreated Npc1$^{nmf164}$ mice at 100 days. Semi-quantitative analysis showed TCF treatment significantly reduced the number of macrophages (FIG. 11). In contrast, administration of Vo alone or HPBCD continued to be associated with abundant macrophage accumulation (FIG. 11). Together these findings suggest that TCF-induced increase of Vo in lungs and reduced inflammation there.

Figures 12A, 12B:
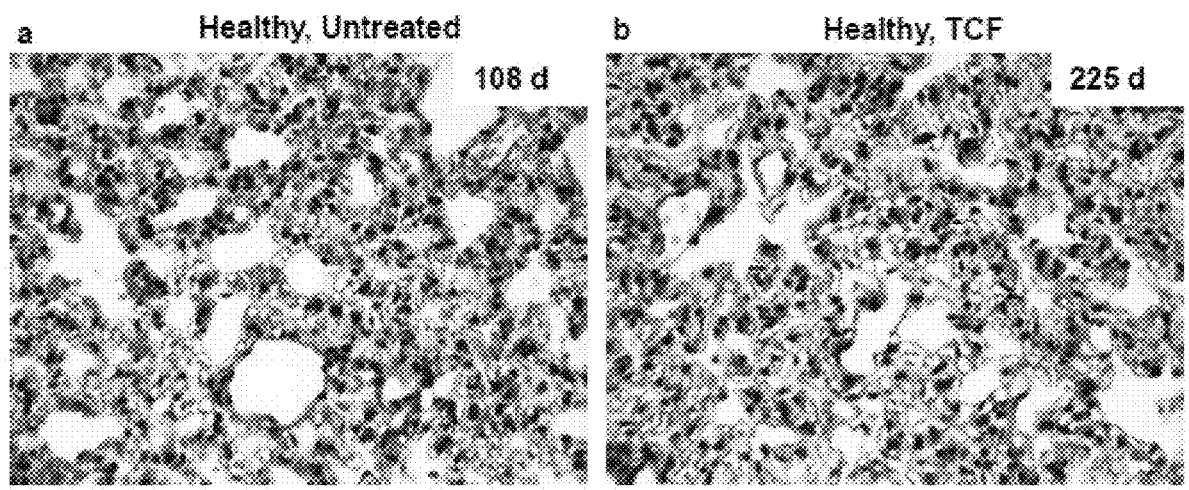
FIGS. 12A-12B show histological analysis of lungs from long term TCF treated mice. Micrographs show H&E stained sections of lungs from (FIG. 12A) untreated and (FIG. 12B) TCF-treated healthy (Npc1$^{+/nmf164}$) mouse at 108 and 225 days respectively. No signs of tissue lesions, immune cell invasion or abnormal pathology were seen in long term TCF-treated mice. The images shown are representative of four untreated (108-109 days) and four TCF-treated healthy mice (age 225-265 days). Images were taken with 40× objective lens.

Long-term chronic treatment with TCF shows no deleterious effect on lung histopathology in healthy control animals. Since our treatment analyses in Npc1$^{nmf164}$ were undertaken at 100 days, the effects of extended TCF administration in control Npc1$^{+/nmf164}$ type animals were assessed at 2-3 times longer periods (200-300 days). We previously reported that analysis of metabolic markers in the plasma failed to reveal toxicity in the liver and kidneys of mice treated once weekly with TCF after 200-300 days[10]. Histological features of liver were also found to be normal[10]. In FIGS. 12A-12B, we show that lungs of Npc1$^{+/nmf164}$ mice at 200-300 days show absence of tissue lesions, immune cell invasion or any abnormal pathology, as determined by H&E staining.

Discussion

Concerns about intrinsic toxicity of HDACi are pertinent for both pan HDACi and inhibitors designed to target a given HDAC, since even a single HDAC can regulate hundreds of genes (and hence the value of synthesizing selective HDACi has been debated). Since neurological treatments may be long term, it is important to learn the effects of extended treatment periods well beyond when efficacy is detectable, especially in the brain. Our data in FIGS. 7A-7C, 8A-8C, and 9A-9B suggest that the TCF enables chronic administration of a therapeutically viable dose of broad spectrum HDACi with no detectable histological changes in key brain regions and neurocognitive/behavioral functions in mice. Purkinje neurons are major neurons that participate in motor control and learning. They can both emit and receive signals and function to regulate the entire cerebellum. Thus, maintenance of Purkinje cells provides a single read out for complex neuronal process in the cerebellum but also communication from the spinal cord and brain stem. Our data showing that the TCF helps preserve Purkinje cells in the NPC disease model, suggests these cells are responsive to HDACi (likely due to elevation of NPC1 protein but possibly also by indirect mechanisms). Therefore, our finding that extended exposure to weekly TCF for 8 to 10 months had no effect on Purkinje neuron staining or count, suggests HDACi administration via the TCF is well tolerated in Purkinje-associated as well as overall cerebellar functions. Similarly, the hippocampus located in the cerebrum and a key region for learning and memory, shows no adverse structural and inflammatory effects despite extended TCF exposure. Although assessment of neurocognitive and behavioral scores do not yield quantitative tissue analyses, they indicate that TCF does not induce symptoms (and therefore processes) of neurodegeneration in wild type mice, even though it can delay appearance of these diseased processes in the NPC mouse model. Finally, findings that the TCF can boost delivery of vorinostat into lungs and reduce recruitment of macrophages into alveolar spaces, suggests that although HPBCD is excluded, vorinostat released from the TCF gains access lungs likely due the plasma exposure. Vo levels delivered to lungs are boosted to sufficiently reduce macrophage levels in Npc1$^{nmf164}$ mice, which significantly expands the potential of the TCF in treating all organ systems expected to affect the progression of NPC. Extended TCF administration showed no ill-effects on lung pathology of normal mice.

To conclude, extended TCF administration failed to induce adverse effects on metabolic parameters, brain, and neurological functions as well as visceral organs including lung, although the TCF shows efficacy in all of these domains in the NPC mouse model. This may appear to be counterintuitive, since Vo is a broad acting HDACi at the transcriptional level with potential to target thousands of genes. However, proteomics studies suggest that changes may be limited to ~200 targets in NPC diseased cells[46]. Moreover, control healthy cells do not show major changes in proteome readouts in response to Vo[46]. One explanation for this difference may be that mechanisms that restore normalcy in diseased cells are distinct from those that maintain homeostasis in normal cells.

REFERENCES

1. Chessum, N., Jones, K., Pasqua, E. & Tucker, M. Recent advances in cancer therapeutics. Progress in medicinal chemistry 54, 1-63, doi:10.1016/bs.pmch.2014.11.002 (2015).
2. Giannini, G., Cabri, W., Fattorusso, C. & Rodriquez, M. Histone deacetylase inhibitors in the treatment of cancer: overview and perspectives. Future Medicinal Chemistry 4, 1439-1460, doi:10.4155/Fmc.12.80 (2012).
3. Mottamal, M., Zheng, S. L., Huang, T. L. & Wang, G. D. Histone Deacetylase Inhibitors in Clinical Studies as Templates for New Anticancer Agents. Molecules 20, 3898-3941, doi:10.3390/molecules20033898 (2015).
4. Falkenberg, K. J. & Johnstone, R. W. Histone deacetylases and their inhibitors in cancer, neurological diseases and immune disorders (vol 13, pg 673, 2014). Nature Reviews Drug Discovery 14, 219-219, doi:10.1038/nrd4579 (2014).
5. Dokmanovic, M., Clarke, C. & Marks, P. A. Histone deacetylase inhibitors: Overview and perspectives. Molecular Cancer Research 5, 981-989, doi:10.1158/1541-7786.Mcr-07-0324 (2007).
6. Xu, W. S., Parmigiani, R. B. & Marks, P. A. Histone deacetylase inhibitors: molecular mechanisms of action. Oncogene 26, 5541-5552, doi:10.1038/sj.onc.1210620 (2007).
7. Di, X.-J., Han, D.-Y., Wang, Y.-J., Chance, M. R. & Mu, T.-W. SAHA Enhances Proteostasis of Epilepsy-Associated α1(A322D)β2γ2 GABA(a) Receptors. Chemistry & biology 20, 10.1016/j.chembiol.2013.1009.1020, doi: 10.1016/j.chembiol.2013.09.020 (2013).
8. Yang, C. et al. Histone deacetylase inhibitors increase glucocerebrosidase activity in Gaucher disease by modulation of molecular chaperones. Proceedings of the National Academy of Sciences of the United States of America 110, 966-971, doi:10.1073/pnas.1221046110 (2013).
9. Calamini, B. & Morimoto, R. I. Protein Homeostasis as a Therapeutic Target for Diseases of Protein Conformation. Current Topics in Medicinal Chemistry 12, 2623-2640 (2012).
10. Alam, M. S., Getz, M. & Haldar, K. Chronic administration of an HDAC inhibitor treats both neurological and systemic Niemann-Pick type C disease in a mouse model. Science translational medicine 8, 326ra323, doi:10.1126/scitranslmed.aad9407 (2016).
11. Vanier, M. T. Niemann-Pick disease type C. Orphanet J Rare Dis 5, 16, doi:10.1186/1750-1172-5-16 (2010).
12. Carstea, E. D. et al. Niemann-Pick C1 disease gene: homology to mediators of cholesterol homeostasis. Science 277, 228-231 (1997).
13. Naureckiene, S. et al. Identification of HE1 as the second gene of Niemann-Pick C disease. Science 290, 2298-2301 (2000).
14. X. Xie, M. S. B., J. M. Shelton, J. A. Richardson, J. L. Goldstein, G. Liang. Amino acid substitution in NPC1 that abolishes cholesterol binding reproduces phenotype of complete NPC1 deficiency in mice. Proc. Natl. Acad. Sci. U.S.A. 108, 15330-15335 (2011).
15. Yu, T. & Lieberman, A. P. Npc1 acting in neurons and glia is essential for the formation and maintenance of CNS myelin. PLoS Genet 9, e1003462, doi:10.1371/journal.pgen.1003462 (2013).
16. Kennedy, B. E., Hundert, A. S., Goguen, D., Weaver, I. C. & Karten, B. Presymptomatic Alterations in Amino Acid Metabolism and DNA Methylation in the Cerebellum of a Murine Model of Niemann-Pick Type C Disease. The American journal of pathology 186, 1582-1597, doi:10.1016/j.ajpath.2016.02.012 (2016).
17. Alobaidy, H. Recent advances in the diagnosis and treatment of niemann-pick disease type C in children: a guide to early diagnosis for the general pediatrician. Int J Pediatr 2015, 816593, doi:10.1155/2015/816593 (2015).
18. Guillemot, N., Troadec, C., de Villemeur, T. B., Clement, A. & Fauroux, B. Lung disease in Niemann-Pick disease. Pediatric pulmonology 42, 1207-1214, doi:10.1002/ppul.20725 (2007).
19. Griese, M. et al. Respiratory disease in Niemann-Pick type C2 is caused by pulmonary alveolar proteinosis. Clinical genetics 77, 119-130, doi:10.1111/j.1399-0004.2009.01325.x (2010).
20. Lyseng-Williamson, K. A. Miglustat: a review of its use in Niemann-Pick disease type C. Drugs 74, 61-74, doi: 10.1007/s40265-013-0164-6 (2014).
21. Nagral, A. Gaucher disease. Journal of clinical and experimental hepatology 4, 37-50, doi:10.1016/j.jceh.2014.02.005 (2014).
22. J. E. Wraith, D. V., E. Jacklin, L. Abel, H. Chadha-Boreham, C. Luzy, R. Giorgino, M. C. Patterson. Miglustat in adult and juvenile patients with Niemann-Pick disease type C: Long-term data from a clinical trial. Mol. Genet. Metab. 99, 351-357 (2010).

23. Pineda, M. et al. Clinical experience with miglustat therapy in pediatric patients with Niemann-Pick disease type C: a case series. Molecular genetics and metabolism 99, 358-366, doi:10.1016/j.ymgme.2009.11.007 (2010).
24. Liu, B. et al. Reversal of defective lysosomal transport in NPC disease ameliorates liver dysfunction and neurodegeneration in the npc1$^{-/-}$ mouse. Proc Natl Acad Sci USA 106, 2377-2382, doi:10.1073/pnas.0810895106 (2009).
25. Ory, D. S. et al. Intrathecal 2-hydroxypropyl-beta-cyclodextrin decreases neurological disease progression in Niemann-Pick disease, type C1: a non-randomised, open-label, phase 1-2 trial. Lancet, doi:10.1016/s0140-6736(17)31465-4 (2017).
26. C. C. Pontikis, C. D. D., S. U. Walkley, F. M. Platt, D. J. Begley. Cyclodextrin alleviates neuronal storage of cholesterol in Niemann-Pick C disease without evidence of detectable blood-brain barrier permeability. J. Inherit. Metab. Dis. 36, 491-498 (2013).
27. Aqul, A. et al. Unesterified cholesterol accumulation in late endosomes/lysosomes causes neurodegeneration and is prevented by driving cholesterol export from this compartment. J Neurosci 31, 9404-9413, doi:10.1523/jneurosci.1317-11.2011 (2011).
28. Vite, C. H. et al. Intracisternal cyclodextrin prevents cerebellar dysfunction and Purkinje cell death in feline Niemann-Pick type C1 disease. Science translational medicine 7, 276ra226, doi:10.1126/scitranslmed.3010101 (2015).
29. Ramirez, C. M. et al. Weekly cyclodextrin administration normalizes cholesterol metabolism in nearly every organ of the Niemann-Pick type C1 mouse and markedly prolongs life. Pediatr Res 68, 309-315, doi:10.1203/00006450-201011001-0060410.1203/PDR.0b013e3181ee4dd2 (2010).
30. Ramirez, C. M. et al. Quantitative role of LAL, NPC2, and NPC1 in lysosomal cholesterol processing defined by genetic and pharmacological manipulations. Journal of lipid research 52, 688-698, doi:10.1194/jlr.M013789 (2011).
31. Kirkegaard, T. et al. Heat shock protein-based therapy as a potential candidate for treating the sphingolipidoses. Science translational medicine 8, 355ra118, doi:10.1126/scitranslmed.aad9823 (2016).
32. Maue, R. A. et al. A novel mouse model of Niemann-Pick type C disease carrying a D1005G-Npc1 mutation comparable to commonly observed human mutations. Human Molecular Genetics 21, 730-750, doi:10.1093/hmg/ddr505 (2012).
33. Fischer, A. H., Jacobson, K. A., Rose, J. & Zeller, R. Hematoxylin and eosin staining of tissue and cell sections. CSH protocols 2008, pdb.prot4986, doi:10.1101/pdb.prot4986 (2008).
34. Norwood, J., Franklin, J. M., Sharma, D. & D'Mello, S. R. Histone deacetylase 3 is necessary for proper brain development. J Biol Chem 289, 34569-34582, doi:10.1074/jbc.M114.576397 (2014).
35. Montgomery, R. L., Hsieh, J., Barbosa, A. C., Richardson, J. A. & Olson, E. N. Histone deacetylases 1 and 2 control the progression of neural precursors to neurons during brain development. Proc Natl Acad Sci USA 106, 7876-7881, doi:10.1073/pnas.0902750106 (2009).
36. Volmar, C.-H. & Wahlestedt, C. Histone deacetylases (HDACs) and brain function. Neuroepigenetics 1, 20-27, doi:https://doi.org/10.1016/j.nepig.2014.10.002 (2015).
37. Venkatraman, A. et al. The histone deacetylase HDAC3 is essential for Purkinje cell function, potentially implicating the use of HDAC inhibitors in SCA1. Human Molecular Genetics 23, 3733-3745, doi:10.1093/hmg/ddu081 (2014).
38. Chitnis, T. & Weiner, H. L. CNS inflammation and neurodegeneration. The Journal of Clinical Investigation 127, doi:10.1172/JCI90609 (2017).
39. Ransohoff, R. M. How neuroinflammation contributes to neurodegeneration. Science 353, 777-783, doi:10.1126/science.aag2590 (2016).
40. Yanjanin, N. M. et al. Linear clinical progression, independent of age of onset, in Niemann-Pick disease, type C. American journal of medical genetics. Part B, Neuropsychiatric genetics: the official publication of the International Society of Psychiatric Genetics 153b, 132-140, doi:10.1002/ajmg.b.30969 (2010).
41. Alam, M. S. et al. Plasma signature of neurological disease in the monogenetic disorder Niemann-Pick Type C. J Biol Chem 289, 8051-8066, doi:10.1074/jbc.M113.526392 (2014).
42. Alam, M. S. et al. Genomic Expression Analyses Reveal Lysosomal, Innate Immunity Proteins, as Disease Correlates in Murine Models of a Lysosomal Storage Disorder. Plos One 7, doi:ARTN e4827310.1371/journal.pone.0048273 (2012).
43. Porter, F. D. et al. Cholesterol oxidation products are sensitive and specific blood-based biomarkers for Niemann-Pick C1 disease. Science translational medicine 2, 56ra81, doi:10.1126/scitranslmed.3001417 (2010).
44. Jiang, X. et al. Development of a bile acid-based newborn screen for Niemann-Pick disease type C. Science translational medicine 8, 337ra363, doi:10.1126/scitranslmed.aaf2326 (2016).
45. Liu, Y. & Bankaitis, V. A. Phosphoinositide phosphatases in cell biology and disease. Prog Lipid Res 49, 201-217 (2010).
46. Subramanian, K., Rauniyar, N., Lavallee-Adam, M., Yates, J. R., 3rd & Balch, W. E. Quantitative Analysis of the Proteome Response to the Histone Deacetylase Inhibitor (HDACi) Vorinostat in Niemann-Pick Type C1 disease. Molecular & cellular proteomics: MCP, doi:10.1074/mcp.M116.064949 (2017).

Each publication, patent, and patent publication cited in this disclosure is incorporated in reference herein in its entirety. The present invention is not intended to be limited to the foregoing examples, but encompasses all such modifications and variations as come within the scope of the appended claims.

The invention claimed is:

1. A method of treating chronic pain in a subject in need thereof, the method comprising administering to the subject a composition comprising (i) a histone deacetylase (HDAC) inhibitor, (ii) a cyclodextrin or salt thereof, and (iii) polyethylene glycol (PEG) or propylene glycol, wherein the composition is provided in a therapeutically effective amount to treat the chronic pain with no metabolic toxicity, wherein the HDAC inhibitor is vorinostat, wherein the cyclodextrin is 2-hydroxypropyl-b-cyclodextrin (HPBCD).

2. The method of claim 1, wherein the polyethylene glycol (PEG) or propylene glycol is polyethylene glycol.

3. The method of claim 1, wherein the composition comprises a molar ratio of HDAC inhibitor:cyclodextrin:PEG of about 1-100:1-1000:1-1000.

4. The method of claim 1, wherein the HDAC inhibitor is present in an administration amount of about 0.1-500 mg/kg, cyclodextrin is present in an administration amount of about 1000-40,000 mg/kg, and the PEG is present in an amount of about 30-60% composition by weight.

5. The method of claim 1, wherein the HDAC inhibitor is vorinostat at an administration amount of about 50 mg/kg, the cyclodextrin is HPBCD at an administration amount of at about 2000 mg/kg, and PEG is about 40-50% composition by weight.

6. The method of claim 1, wherein the chronic pain comprises one or more of, chronic nociceptive pain, chronic neuropathic pain, chronic inflammatory pain, arthritis pain, fibromyalgia, breakthrough pain, persistent pain, hyperalgesia, allodynia, central sensitization, peripheral sensitization, disinhibition and augmented facilitation, or cancer pain.

7. A method of reducing or inhibiting one or more symptoms of chronic pain, the method comprising administering to the subject a composition comprising (i) a histone deacetylase (HDAC) inhibitor, (ii) a cyclodextrin or salt thereof, and (iii) polyethylene glycol (PEG) or propylene glycol, wherein the composition is provided in a therapeutically effective amount to reduce or inhibit one or more symptom of chronic pain with no metabolic toxicity,
wherein the HDAC inhibitor is vorinostat, wherein the cyclodextrin is 2-hydroxypropyl-b-cyclodextrin (HPBCD).

8. The method of claim 7, wherein the polyethylene glycol (PEG) or propylene glycol is polyethylene glycol.

9. The method of claim 7, wherein the composition comprises a molar ratio of HDAC inhibitor:cyclodextrin:PEG of about 1-100:1-1000:1-1000.

10. The method of claim 7, wherein the HDAC inhibitor is present in an administration amount of about 0.1-500 mg/kg, cyclodextrin is present in an administration amount of about 1000-40,000 mg/kg, and the PEG is present in an amount of about 30-60% composition by weight.

11. The method of claim 7, wherein the HDAC inhibitor is vorinostat at an administration amount of about 50 mg/kg, the cyclodextrin is HPBCD at an administration amount of at about 2000 mg/kg, and PEG is about 40-50% composition by weight.

12. The method of any one of claim 7, wherein the chronic pain comprises one or more of, chronic nociceptive pain, chronic neuropathic pain, chronic inflammatory pain, fibromyalgia, breakthrough pain, persistent pain, hyperalgesia, allodynia, central sensitization, peripheral sensitization, disinhibition and augmented facilitation, or cancer pain.

* * * * *